United States Patent
Ishige et al.

(10) Patent No.: US 10,018,585 B2
(45) Date of Patent: Jul. 10, 2018

(54) ELECTROLYTE CONCENTRATION MEASURING APPARATUS AND MEASURING METHOD USING SAME

(71) Applicant: Hitachi High-Technologies Corporation, Minato-ku, Tokyo (JP)

(72) Inventors: Yu Ishige, Tokyo (JP); Masao Kamahori, Tokyo (JP); Atsushi Kishioka, Tokyo (JP); Tetsuyoshi Ono, Tokyo (JP); Masafumi Miyake, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 264 days.

(21) Appl. No.: 14/888,271

(22) PCT Filed: Apr. 10, 2014

(86) PCT No.: PCT/JP2014/060417
§ 371 (c)(1),
(2) Date: Oct. 30, 2015

(87) PCT Pub. No.: WO2014/181632
PCT Pub. Date: Nov. 13, 2014

(65) Prior Publication Data
US 2016/0054257 A1   Feb. 25, 2016

(30) Foreign Application Priority Data
May 7, 2013 (JP) .................................. 2013-097658

(51) Int. Cl.
*G01N 27/413* (2006.01)
*G01N 27/333* (2006.01)
(Continued)

(52) U.S. Cl.
CPC ......... *G01N 27/413* (2013.01); *G01N 27/021* (2013.01); *G01N 27/04* (2013.01);
(Continued)

(58) Field of Classification Search
CPC ............. G01N 27/413; G01N 27/4166; G01N 27/4035; G01N 27/021; G01N 27/04; G01N 27/333; G01N 33/492
See application file for complete search history.

(56) References Cited

U.S. PATENT DOCUMENTS

| 7,297,241 B2 | 11/2007 | Kontschieder et al. |
| 2003/0152486 A1 | 8/2003 | Yamashita et al. |

(Continued)

FOREIGN PATENT DOCUMENTS

| CN | 1032980 A | 5/1989 |
| CN | 102313770 A | 1/2012 |

(Continued)

OTHER PUBLICATIONS

Machine Translation of JP 2003-207481 A (Year: 2003).*
(Continued)

*Primary Examiner* — J. Christopher Ball
(74) *Attorney, Agent, or Firm* — Crowell & Moring LLP

(57) ABSTRACT

An electrolyte concentration measuring apparatus is provided with: a plurality of ion selective electrodes and one reference electrode; a sample introduction unit that introduces a sample solution to the plurality of ion selective electrodes and the reference electrode; a potential measuring unit that measures a voltage between the plurality of ion selective electrodes and the reference electrode; and a resistance measuring unit that measures a direct-current resistance of the plurality of ion selective electrodes.

13 Claims, 25 Drawing Sheets

(51) Int. Cl.
  *G01N 33/49* (2006.01)
  *G01N 27/02* (2006.01)
  *G01N 27/04* (2006.01)
  *G01N 27/403* (2006.01)
  *G01N 27/416* (2006.01)

(52) U.S. Cl.
  CPC ....... *G01N 27/333* (2013.01); *G01N 27/4035* (2013.01); *G01N 27/4166* (2013.01); *G01N 33/492* (2013.01)

(56) References Cited

U.S. PATENT DOCUMENTS

| | | | |
|---|---|---|---|
| 2007/0231882 | A1 | 10/2007 | Kamahori et al. |
| 2008/0318243 | A1 | 12/2008 | Haga et al. |
| 2011/0276278 | A1 | 11/2011 | Ishige et al. |

FOREIGN PATENT DOCUMENTS

| | | | |
|---|---|---|---|
| JP | 5-209857 | A | 8/1993 |
| JP | 6-258277 | A | 9/1994 |
| JP | 7-239313 | A | 9/1995 |
| JP | 10-246720 | A | 9/1998 |
| JP | 2001-174430 | A | 6/2001 |
| JP | 2001-235443 | A | 8/2001 |
| JP | 2002-39989 | A | 2/2002 |
| JP | 2003-207476 | A | 7/2003 |
| JP | 2003-207481 | A | 7/2003 |
| JP | 2004-85566 | A | 3/2004 |
| JP | 2009-92854 | A | 4/2009 |
| WO | WO 2010/052867 | A1 | 5/2010 |

OTHER PUBLICATIONS

D. Diamond, et al. "Resistance measurements as a simple diagnostic tool for ion-selective electrode performance" Electroanalysis, vol. 2, No. 2, 1990, p. 113-117.*

Fluke 8060A True-rms Multimeter Instruction Manual. (Year: 1997).*

International Search Report (PCT/ISA/210) issued in counterpart International Application No. PCT/JP2014/060417 dated Jun. 24, 2014, with English translation (Five (5) pages).

Umezawa, et al., "Potentiometric Selectivity Coefficients of Ion-Selective Electrodes—Part I. Inorganic Cations", Pure Appl. Chem., vol. 72, No. 10, pp. 1851-2082, 2000, (Two Hundred and Thirty Two (232) pages).

Umezawa, et al., "Potentiometric Selectivity Coefficients of Ion-Selective Electrodes—Part II. Inorganic Anions", Pure Appl. Chem., vol. 74, No. 6, pp. 923-994, 2002, (Seventy Two (72) pages).

Chinese Office Action issued in counterpart Chinese Application No. 201480024768.0 dated Nov. 16, 2016 (four (4) pages).

Chinese Office Action issued in counterpart Chinese Application No. 201480024768.0 dated May 17, 2017 with English translation (19 pages).

* cited by examiner

ELECTROLYTE CONCENTRATION MEASURING APPARATUS AND MEASURING METHOD USING SAME

TECHNICAL FIELD

The present invention relates to an electrolyte concentration measuring apparatus for measuring the electrolyte concentration in a solution, and a measuring method using the apparatus.

BACKGROUND ART

An ion selective electrode (ISE) is used for determining the quantity of an ion to be measured in a sample. For example, the ion selective electrode is immersed, together with a reference electrode, in a sample solution containing an electrolyte. In this state, a potential difference between the electrodes is measured to determine the quantity of the ion to be measured in the sample. Due to its simplicity, the ion selective electrode is widely utilized in analysis fields. In the medical field, the ion selective electrode is used for clinical test, and may be mounted not only in a dedicated machine for electrolyte concentration measurement but also in an automated clinical analyzer or a critical care analyzer as an electrolyte concentration measuring unit.

Particularly, high measurement accuracy is required in the medical field, and various measures have been devised to improve measurement accuracy. Generally, the ion selective electrode is a regularly replaced component, and its replacement is recommended after a certain number of times or a certain period of use. As a method for determining a defect or degradation of the ion selective electrode, Patent Literature 1 and Patent Literature 2 disclose methods of measuring the resistance value of the ion selective electrode.

CITATION LIST

Patent Literature

Patent Literature 1: JP 2009-092854 A
Patent Literature 2: JP 2003-207481 A
Patent Literature 3: JP 2003-207476 A
Patent Literature 4: JP H05-209857 A

Non Patent Literature

Non Patent Literature 1: Pure Appl. Chem., Vol. 72, No. 10, pp. 1851-2082, 2000
Non Patent Literature 2: Pure Appl. Chem., Vol. 74, No. 6, pp. 923-994, 2002

SUMMARY OF THE INVENTION

Technical Problems

It has been learned that when the resistance value of the ion selective electrode is measured in the electrolyte concentration measuring apparatus, sufficient accuracy cannot be obtained by the conventional methods according to Patent Literature 1 and Patent Literature 2.

As described in Patent Literature 1, alternating-current measurement is subject to the influence of parasitic capacity and apt to underestimate the resistance. Accordingly, for the purpose of measuring the resistance that is increased by degradation, it is suitable to measure direct-current resistance on which the influence of parasitic capacity is small. However, in Patent Literature 1, because direct-current voltage measurement is performed for electrolyte concentration measurement simultaneously with the measurement of alternating-current resistance, direct-current resistance measurement cannot be performed.

In Patent Literature 2, it is described that, while resistance measurement can be performed either by direct-current or alternating-current, alternating-current is preferable. This is believed due to the use of a platinum electrode for resistance measurement. While platinum electrodes are generally used for alternating-current resistance measurement, they cannot be considered the most suitable for direct-current resistance measurement. For high-accuracy direct-current resistance measurement, it is necessary that there be a stable interface potential produced between the platinum electrode and the solution in contact with the platinum electrode. However, the interface potential lacks stability and easily varies, and the variations may cause a direct-current resistance measurement error. In addition, if the surface of the platinum electrode is contaminated by protein and the like in the sample, the error becomes more pronounced. In alternating-current resistance measurement, this problem is not often encountered as the interface is represented by an electric double layer capacitor.

The present invention provides an apparatus that measures the direct-current resistance value of an ion selective electrode with high accuracy, and a measuring method using the apparatus.

Solution to Problem

In order to solve the problems, the configurations set forth in the claims are adopted, for example. While the present application includes a plurality of means for solving the problems, one example provides an electrolyte concentration measuring apparatus that includes a plurality of ion selective electrodes and one reference electrode; a sample introduction unit that introduces a sample solution into the plurality of ion selective electrodes and the reference electrode; a potential measuring unit that measures a voltage between the plurality of ion selective electrodes and the reference electrode; and a resistance measuring unit that measures a direct-current resistance of the plurality of ion selective electrodes.

Another example provides a method of measuring a direct-current resistance of a plurality of ion selective electrodes in an electrolyte concentration measuring apparatus provided with the plurality of ion selective electrodes and one reference electrode. The method includes a first step of measuring an electromotive force between at least one of the plurality of ion selective electrodes and the reference electrode; a second step of measuring a voltage and a current between the at least one of the plurality of ion selective electrodes and the reference electrode; and a third step of determining the direct-current resistance from the electromotive force, the voltage, and the current.

Advantageous Effects of Invention

According to the present invention, by measuring the direct-current resistance of an ion selective electrode, the influence of parasitic capacity that has been the cause of resistance underestimation in alternating-current resistance measurement can be suppressed. By measuring the direct-current resistance between two electrodes including the reference electrode and the ion selective electrode, the direct-current resistance can be stably measured because the potential at the interface of a solution and the reference electrode or the ion selective electrode is stable.

Additional features relating to the present invention will become apparent from the following description in the Description and the attached drawings. Problems, configurations, and effects other than those mentioned above will become apparent from the following description of embodiments.

DESCRIPTION OF EMBODIMENTS

In the following, embodiments of the present invention will be described with reference to the attached drawings. While the attached drawings illustrate specific embodiments in accordance with the principle of the present invention, the embodiments are provided for facilitating an understanding of the present invention and are not to be used for interpreting the present invention in a limited sense.

Figure 1A:
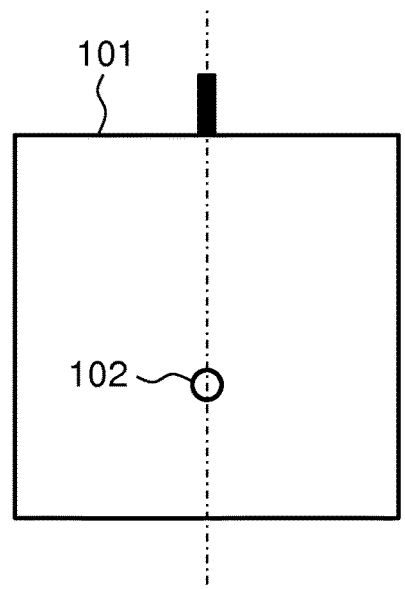
FIG. 1A is a schematic diagram of an example of an ion selective electrode, in a plane perpendicular to a flow passageway.
Figure 1B:
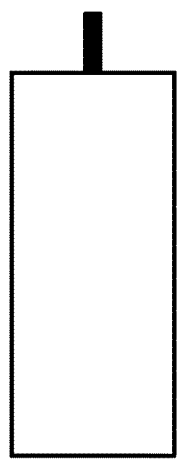
FIG. 1B is schematic diagram of the example of the ion selective electrode in a plane parallel to the flow passageway.
Figure 1C:
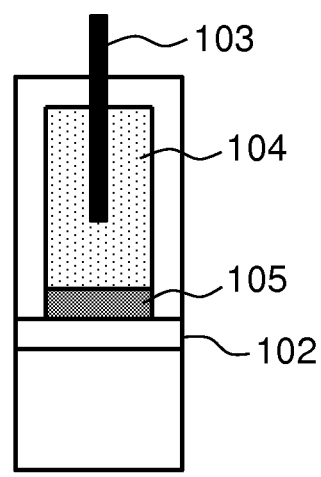
FIG. 1C is a cross-sectional view taken along a chain line of FIG. 1A.

FIG. 1A is a schematic diagram of an example of an ion selective electrode, shown in a plane perpendicular to a flow passageway. FIG. 1B illustrates a plane parallel with the flow passageway. FIG. 1C is a cross-sectional view taken along a chain line of FIG. 1A.

In a cartridge 101 of the ion selective electrode, a flow passageway 102 is passed. The flow passageway 102 is in contact with a sensitive membrane 105. On the opposite side from the flow passageway 102 across the sensitive membrane 105, internal solution 104 is filled. The internal solution 104 is in contact with a silver-silver chloride electrode 103. The silver-silver chloride electrode 103 also serves as a terminal.

In the case of a cation selective electrode for sodium, potassium, calcium, magnesium and the like, the sensitive membrane 105 may include the membranes described in Non Patent Literature 1. In the case of an anion selective electrode for chlorine, carbonic acid, thiocyanogen, nitric acid, hydroxide ion, phosphoric acid, sulfuric acid, iodine and the like, the sensitive membrane 105 may include silver halides such as silver chloride and silver bromide, or an ion-exchange membrane (Patent Literature 3), as well as the membranes described in Non Patent Literature 2. In the case of a reference electrode, the sensitive membrane 105 may include porous glass, ceramic, and the like.

Figure 2:
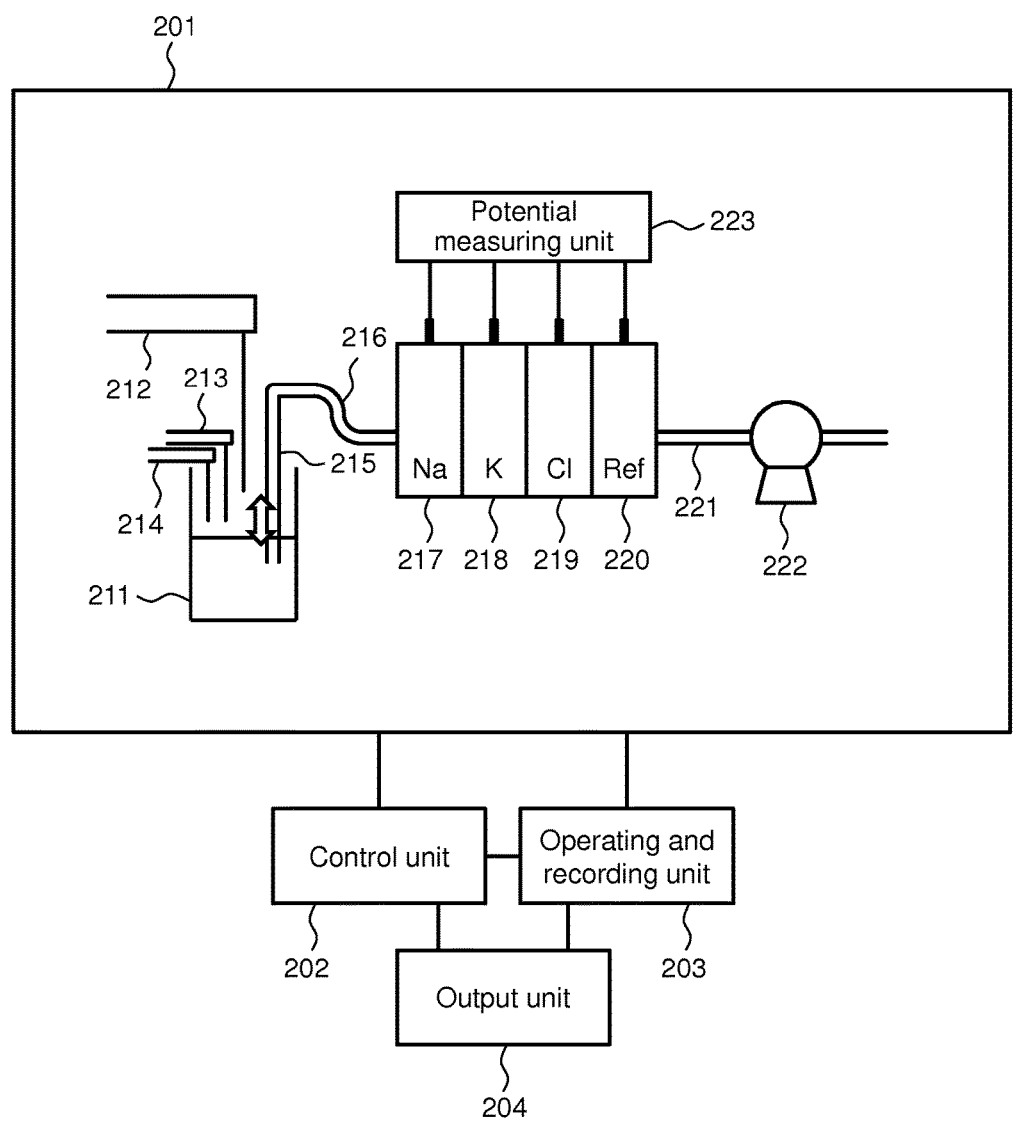
FIG. 2 is a schematic diagram of an example of an electrolyte concentration measuring apparatus.

FIG. 2 is a schematic diagram of an example of an electrolyte concentration measuring apparatus using the ion selective electrode of FIG. 1. The electrolyte concentration measuring apparatus is provided with a measuring unit 201; a control unit 202; an operating and recording unit 203; and an output unit 204. The control unit 202, the operating and recording unit 203, and the output unit 204 are connected to the measuring unit 201.

The control unit 202 controls the constituent elements of the measuring unit 201, which will be described later. The operating and recording unit 203 calculates the ion concentration of a measuring object on the basis of a potential and the like measured by the measuring unit 201. The output unit 204 may include a display or a printer and the like.

The control unit 202 and the operating and recording unit 203 may be implemented using a general-purpose computer, or may be implemented as functions of a program executed on a computer. Namely, the processes of the control unit 202 and the operating and recording unit 203 that will be described below may be implemented by storing program codes in a storage unit such as a memory, and having each program code executed by a processor such as a central processing unit (CPU). The control unit 202 and the operating and recording unit 203 may be configured using hardware such as dedicated circuit substrates.

The measuring unit 201 includes a dilution tank 211; a specimen dispensing nozzle 212; a diluting fluid dispensing nozzle 213; an internal standard solution dispensing nozzle 214; a sample solution suction nozzle 215; a piping 216; a sodium ion selective electrode 217; a potassium ion selective electrode 218; a chlorine ion selective electrode 219; a reference electrode 220; a piping 221; a pump 222; and a potential measuring unit 223. In the measuring unit 201, the sample solution suction nozzle 215, the piping 216, the piping 221, and the pump 222 are used as a sample introduction unit for introducing a sample solution containing electrolyte.

In the measuring unit 201, the sample introduction unit is used to introduce the sample solution into the flow passageways of the ion selective electrodes 217 to 219 and the reference electrode 220. With the sample solution having been introduced, potential differences between the electrodes are measured. In the following, a detailed configuration will be described.

The specimen dispensing nozzle 212 dispenses and discharges a specimen, such as blood or urine, into the dilution tank 211. The diluting fluid dispensing nozzle 213 dispenses and discharges a diluting fluid into the dilution tank 211. The internal standard solution dispensing nozzle 214 dispenses and discharges an internal standard solution into the dilution tank 211. The sample solution suction nozzle 215 can be moved up and down and suctions the solution in the dilution tank 211 using the driving force of the pump 222. The suctioned solution is introduced via the piping 216 into the flow passageways of the electrodes 217 to 220, and is further discarded via the piping 221. The terminals of the ion selective electrodes 217, 218, and 219 and the reference electrode 220 are connected to the potential measuring unit 223.

Figure 3:
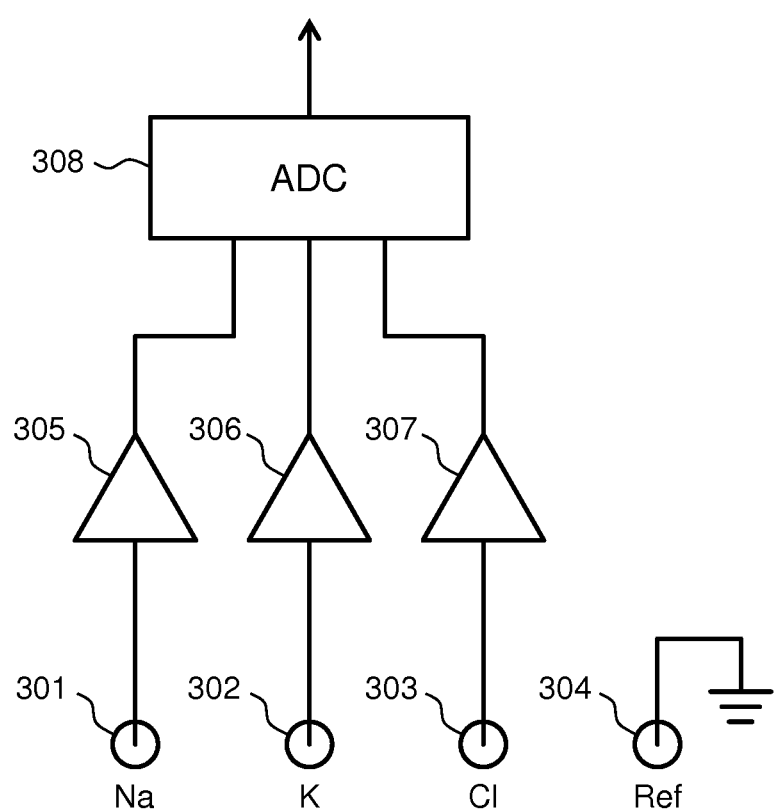
FIG. 3 is a schematic diagram of an example of a potential measuring unit.

FIG. 3 is a circuit diagram of an example of the potential measuring unit 223. A terminal 304 to which the reference electrode 220 is connected is connected to ground. Terminals 301, 302, and 303 to which the other ion selective electrodes 217, 218, and 219 are connected are connected to amplifiers 305, 306, and 307 with an input impedance on the order of 1 GΩ. Outputs from the amplifiers 305, 306, and 307 are input to an analog-digital converter (AD converter) 308, and the AD converter 308 outputs a digital value.

Figure 4:
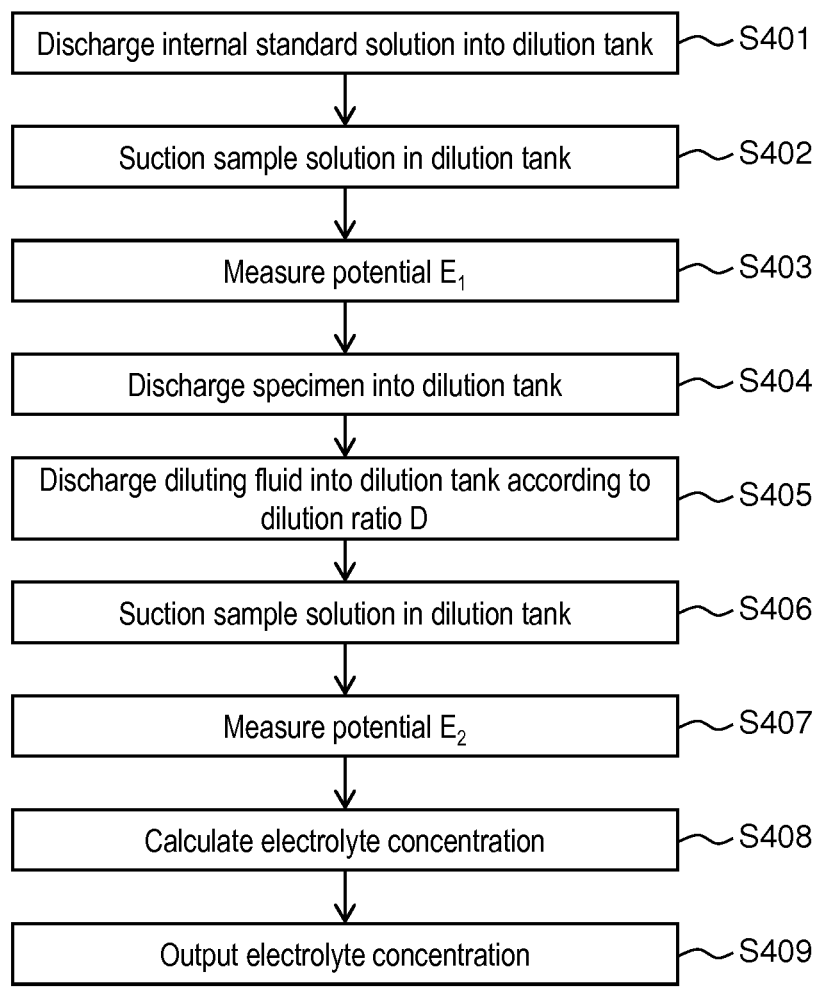
FIG. 4 shows an example of a flowchart of electrolyte concentration measurement.

FIG. 4 shows an example of a flowchart of electrolyte concentration measurement using the electrolyte concentration measuring apparatus of FIG. 2. The process of FIG. 4 is mainly controlled by the control unit 202.

First, using the internal standard solution dispensing nozzle 214, the internal standard solution is discharged into the dilution tank 211 (S401). Then, the sample solution suction nozzle 215 and the pump 222 are used to suction the internal standard solution in the dilution tank 211 (S402). As a result, the flow passageways of the electrodes 217 to 220 are filled with the internal standard solution.

Next, using the potential measuring unit 223, the potentials of the ion selective electrodes 217 to 219 with reference to the reference electrode 220 are measured (S403). Herein, the potentials of the electrodes 217 to 219 are $E_{1,n}$ (n is the respective ion species). Then, the specimen dispensing nozzle 212 is used to discharge the specimen into the dilution tank 211 (S404).

The diluting fluid dispensing nozzle 213 is then used to discharge the diluting fluid into the dilution tank 211 (S405), whereby the specimen is diluted according to a ratio D of the amount of specimen to the amount of diluting fluid. The sample solution suction nozzle 215 and the pump 222 are then used to suction the sample solution in the dilution tank 211 (S406), whereby the flow passageways of the electrodes 217 to 220 are filled with the sample solution.

Then, using the potential measuring unit 223, the potentials of the electrodes 217 to 219 with reference to the reference electrode 220 are measured (S407). Herein, the potentials of the electrodes 217 to 219 are $E_{2,n}$. The operating and recording unit 203 is then used to calculate the concentration of the ion to be measured in the specimen (S408). Specifically, from $E_{1,n}$, $E_{2,n}$, D and the concentration $c_{IS,n}$ of the ion to be measured in the internal standard solution, the concentration $c_n$ of the ion to be measured in the specimen is calculated according to the following expression, which is based on the Nernst equation.

$$c_n = Dc_{IS,n} \exp\left(\frac{zF}{RT}(E_{2,n} - E_{1,n})\right) \qquad \text{[Expression 1]}$$

(z: valence of ion to be measured, F: Faraday constant, R: gas constant, T: absolute temperature)

Finally, the concentration calculated in S408 is output by the output unit 204 in the form of a screen output, printed characters and the like (S409).

The diluting fluid may include a fluid that does not contain the ion to be measured, such as a tris-borate buffer or a bis-tris-borate buffer (see Patent Literature 4, for example). The internal standard solution may include a solution of the ions to be measured of the order of the blood level reference values, such as 140 mM of sodium, 4 mM of potassium, and 100 mM of chlorine, as an assumed specimen, which is then diluted with the diluting fluid at the dilution ratio D.

Figure 5:
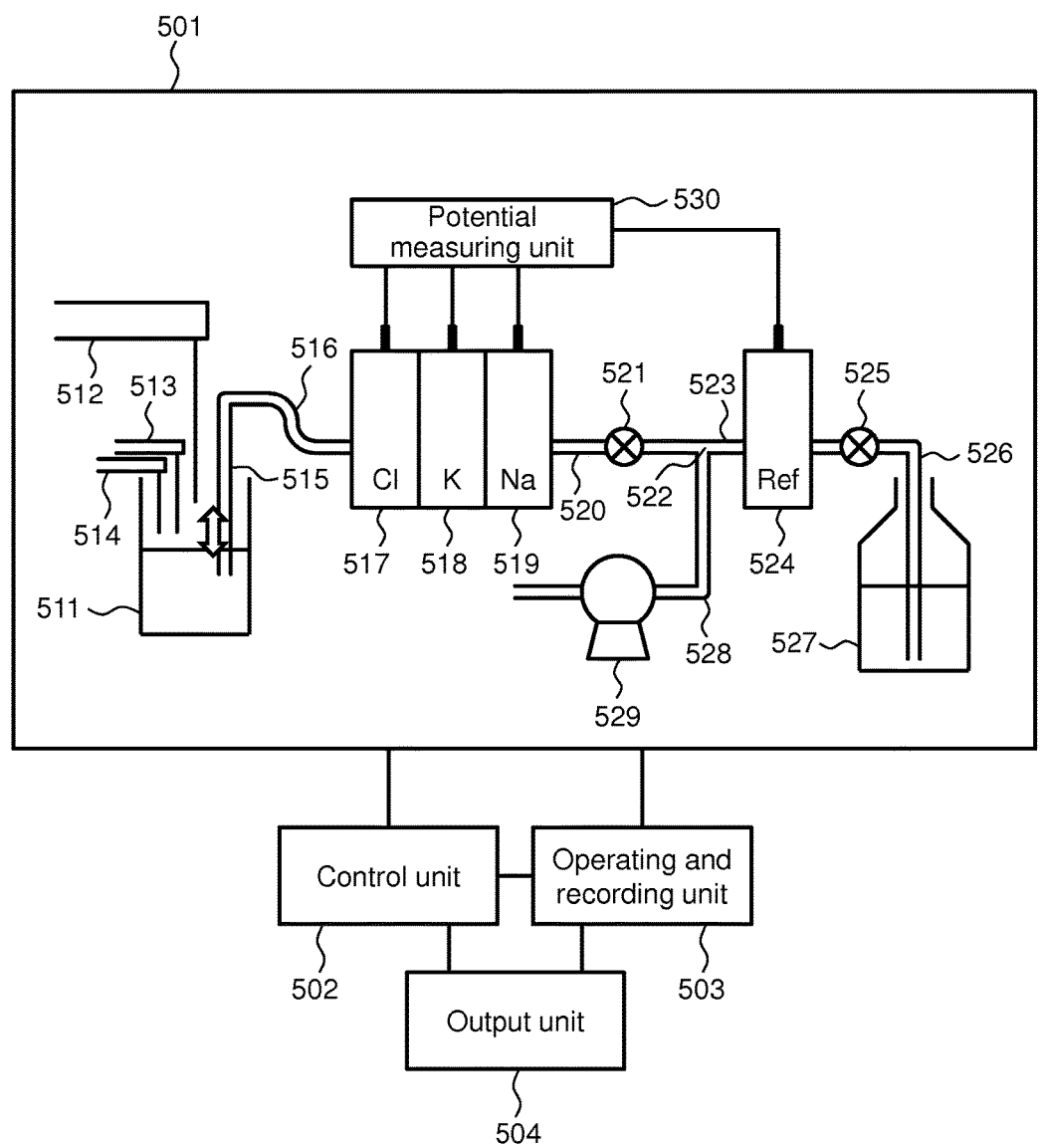
FIG. 5 is a schematic diagram of another example of the electrolyte concentration measuring apparatus.

FIG. 5 is a schematic diagram of another example of the electrolyte concentration measuring apparatus using the ion selective electrode of FIG. 1. The electrolyte concentration measuring apparatus is provided with a measuring unit 501; a control unit 502; an operating and recording unit 503; and an output unit 504. The control unit 502, the operating and recording unit 503, and the output unit 504 are connected to the measuring unit 501.

The control unit 502 controls the constituent elements of the measuring unit 501, which will be described below. The operating and recording unit 503 calculates the ion concentration of the measuring object on the basis of the potential and the like measured by the measuring unit 501. The output unit 504 may include a display or a printer.

As in the case of FIG. 2, the control unit 502 and the operating and recording unit 503 may be implemented using a general-purpose computer, or may be implemented as functions of a program executed on a computer. Namely, the processes of the control unit 502 and the operating and recording unit 503 as will be described below may be implemented by storing program codes in a storage unit such as a memory, and having each program code executed by a processor, such as a CPU. The control unit 502 and the operating and recording unit 503 may be configured using hardware, such as dedicated circuit substrates.

The measuring unit 501 includes a dilution tank 511; a specimen dispensing nozzle 512; a diluting fluid dispensing nozzle 513; an internal standard solution dispensing nozzle 514; a sample solution suction nozzle 515; a piping 516; a chlorine ion selective electrode 517; a potassium ion selective electrode 518; a sodium ion selective electrode 519; a piping 520; a valve 521; a junction 522; a piping 523; a reference electrode 524; a valve 525; a piping 526; a reference solution 527; a piping 528; a pump 529; and a potential measuring unit 530.

In the measuring unit 501, the sample solution suction nozzle 515, the piping 516, the piping 520, the valve 521, the junction 522, the piping 523, the valve 525, the piping 526, the piping 528, and the pump 529 are used as a sample introduction unit for introducing the sample solution and the reference solution. In the measuring unit 501, the sample introduction unit is used to introduce the sample solution into the flow passageways of the ion selective electrodes 517 to 519, and to introduce the reference solution 527 into the flow passageway of the reference electrode 524. In this state, potential differences between the electrodes are measured. A detailed configuration will be described below.

The specimen dispensing nozzle 512 dispenses and discharges the specimen, such as blood or urine, into the dilution tank 511. The diluting fluid dispensing nozzle 513 dispenses and discharges the diluting fluid into the dilution tank 511. The internal standard solution dispensing nozzle 514 dispenses and discharges the internal standard solution into the dilution tank 511.

The sample solution suction nozzle 515 can be moved up and down and suctions the solution in the dilution tank 511 by the driving force of the pump 529. When the valve 521 is opened and the valve 525 is closed, the solution suctioned by the sample solution suction nozzle 515 is introduced via the piping 516 to the flow passageways of the ion selective electrodes 517 to 519, and is further discarded via the piping 520, the junction 522, and the piping 528.

When the valve 521 is closed and the valve 525 is opened, as the pump 529 is driven, the reference solution 527 is suctioned via the piping 526 and introduced into the flow passageway of the reference electrode 524. The suctioned reference solution 527 is further discarded via the piping 523, the junction 522, and the piping 528.

The terminals of the ion selective electrodes 517 to 519 and the reference electrode 524 are connected to the potential measuring unit 530. The potential measuring unit 530 may be similar to the one of FIG. 3. The reference electrode 524 may include an ion selective electrode in addition to the reference electrode using porous glass or ceramic as described above with reference to FIG. 2, and the electrolyte concentration in the reference solution 527 corresponding to the ion selective electrode may be made constant.

Figure 6:
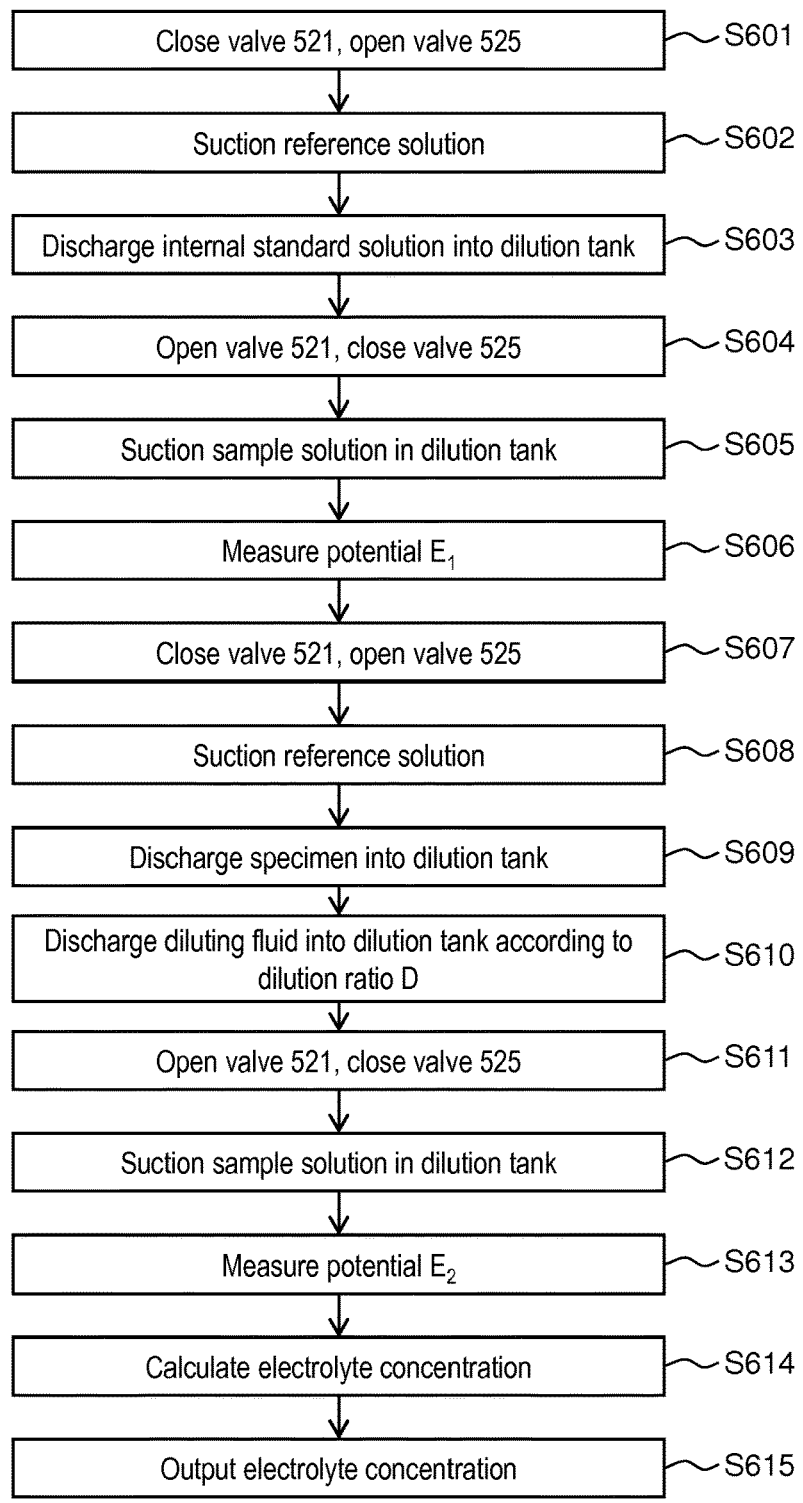
FIG. 6 shows an example of a flowchart of electrolyte concentration measurement.

FIG. 6 shows an example of a flowchart of electrolyte concentration measurement using the electrolyte concentration measuring apparatus of FIG. 5. The process of FIG. 6 is mainly controlled by the control unit 502.

First, the valve 521 is closed and the valve 525 is opened (S601), and the reference solution 527 is suctioned using the pump 529 and the piping 526 (S602). Thereby, the flow passageway of the reference electrode 524, the piping 523, and the junction 522 are filled with the reference solution 527.

Then, using the internal standard solution dispensing nozzle 514, the internal standard solution is discharged into the dilution tank 511 (S603). The valve 521 is then opened and the valve 525 is closed (S604), and the sample solution suction nozzle 515 and the pump 529 are used to suction the internal standard solution in the dilution tank 511 (S605). Thereby, the flow passageways of the electrodes 517 to 519, the piping 520, and the junction 522 are filled with the internal standard solution. At this time, because the ion selective electrodes 517 to 519 and the reference electrode 524 are connected by the pipings 520 and 523 and the junction 522 which are filled with the solution, the potential $E_{1,n}$ of the ion selective electrodes 517 to 519 with reference to the reference electrode 524 are measured using the potential measuring unit 530 (S606).

Similarly, the valve 521 is closed and the valve 525 is opened (S607), and the reference solution 527 is suctioned using the pump 529 and the piping 526 (S608). Then, using the specimen dispensing nozzle 512, the specimen is discharged into the dilution tank 511 (S609). Thereafter, the diluting fluid dispensing nozzle 513 is used to discharge the diluting fluid into the dilution tank 511 (S610). As a result, the specimen is diluted according to the ratio D of the amount of specimen and the amount of diluting fluid.

Then, the valve 521 is opened and the valve 525 is closed (S611), and the sample solution suction nozzle 515 and the pump 529 are used to suction the sample solution in the dilution tank 511 (S612). Thereby, the flow passageways of the ion selective electrodes 517 to 519, the piping 520, and the junction 522 are filled with the sample solution. At this time, the potential $E_{2,n}$ of the ion selective electrodes 517 to 519 with reference to the reference electrode 524 is measured using the potential measuring unit 530 (S613).

Next, using the operating and recording unit 503, the concentration of the ion to be measured in the specimen is calculated (S614). Specifically, based on $E_{1,n}$, $E_{2,n}$, D and the concentration $c_{IS,n}$ of the ion to be measured in the internal standard solution, the concentration of the ion to be measured $c_n$ in the specimen is calculated according to the following expression based on the Nernst equation.

$$c_n = Dc_{IS,n} \exp\left(\frac{zF}{RT}(E_{2,n} - E_{1,n})\right) \qquad \text{[Expression 2]}$$

(z: valence of the ion to be measured, F: Faraday constant, R: gas constant, T: absolute temperature)

Finally, the concentration calculated in S614 is output by the output unit 504 in the form of a screen output, printed characters or the like (S615).

First Embodiment

Figure 7:
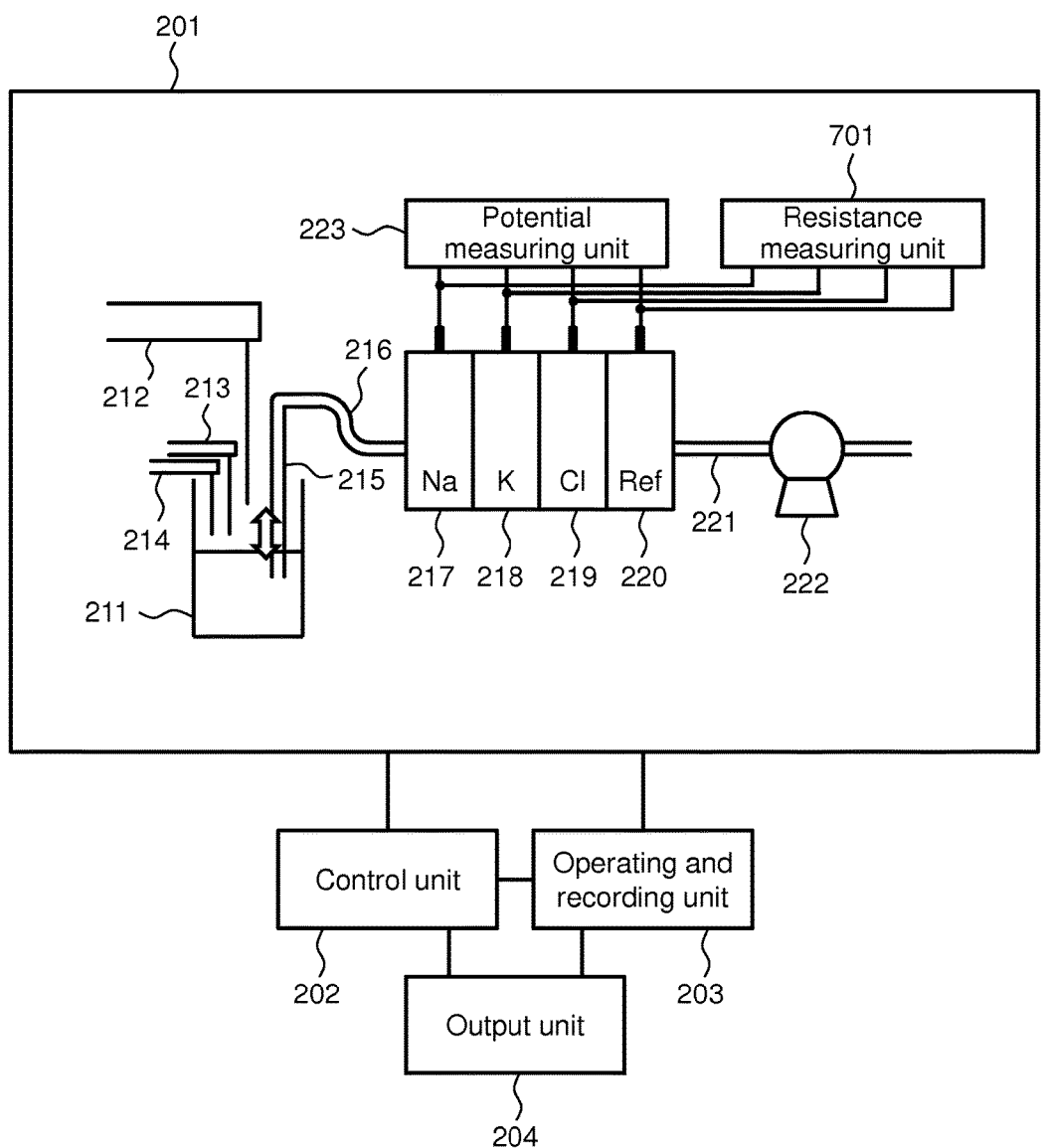
FIG. 7 is a schematic diagram of a first embodiment of a configuration for measuring the resistance value of the ion selective electrodes.

FIG. 7 is a schematic diagram of an example of the configuration for measuring the resistance value of the ion selective electrodes in the electrolyte concentration measuring apparatus of FIG. 2. Compared to the configuration of FIG. 2, a resistance measuring unit 701 is added. The resistance measuring unit 701 is electrically connected to the terminals of the electrodes 217 to 220.

Figure 8:
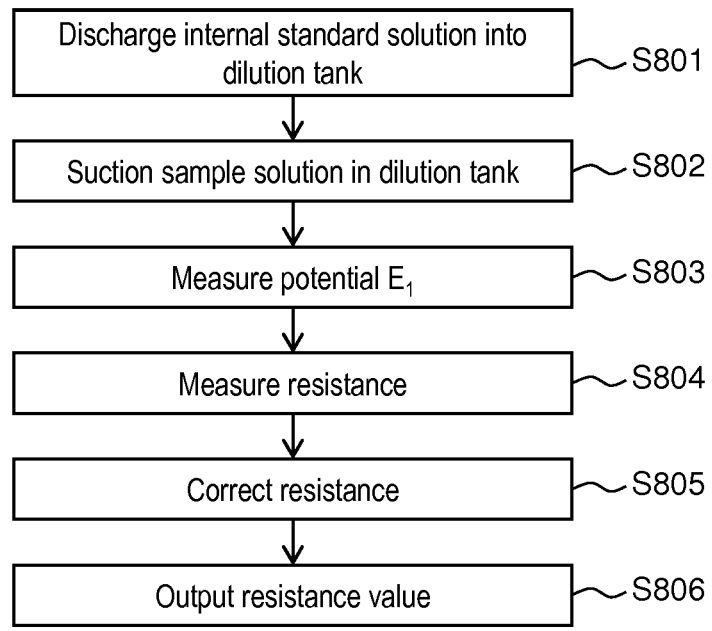
FIG. 8 shows an example of a flowchart of measurement of the resistance value of the ion selective electrodes.

FIG. 8 shows an example of a flowchart of measurement of the resistance value of the ion selective electrodes using the electrolyte concentration measuring apparatus of FIG. 7. The process of FIG. 8 is mainly controlled by the control unit 202. The measurement of the direct-current resistance includes: measuring the electromotive force between at least one of the plurality of ion selective electrodes 217 to 219 (hereafter referred to as a measuring object electrode) and the reference electrode 220; measuring a voltage and a current between the measuring object electrode and the reference electrode 220; and determining a direct-current resistance from the electromotive force, the voltage, and the current. Details will be described in the following.

First, using the internal standard solution dispensing nozzle 214, the internal standard solution is discharged into the dilution tank 211 (S801). Then, the sample solution suction nozzle 215 and the pump 222 are used to suction the internal standard solution in the dilution tank 211 (S802). As a result, the flow passageways of the electrodes 217 to 220 are filled with the internal standard solution.

The potential measuring unit 223 is then used to measure the potentials of the electrodes 217 to 219 with reference to the reference electrode 220 (S803). Herein, the potentials of the ion selective electrodes 217 to 219 are $E_{1,n}$ (n is the respective ion species). Then, using the resistance measuring unit 701, the resistance values between the terminal of the reference electrode 220 and the respective terminals of the electrodes 217 to 219 are measured (S804).

Figure 9:
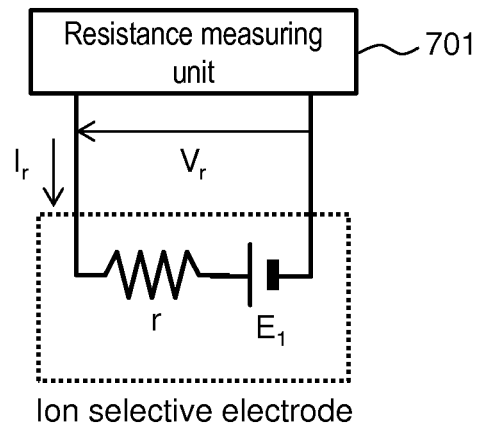
FIG. 9 shows an example of an equivalent circuit for the measurement of the resistance value of the ion selective electrode according to the first embodiment.

FIG. 9 shows an example of the equivalent circuit for the measurement of the resistance value of the ion selective electrode. The resistance measuring unit 701 that measures the direct-current resistance is connected to the ion selective electrodes 217 to 219 and the reference electrode 220 that are used for the electrolyte concentration measurement. The measurement of the direct-current resistance is performed between any two of the electrodes 217 to 220 including the reference electrode 220. In the present example, the two electrodes are the reference electrode 220 and any of the ion selective electrodes 217 to 219 desired to be measured.

The direct-current resistance may be measured by a method whereby current is measured while a certain voltage is being applied, or a method whereby voltage is measured in the presence of a certain current flow. In either method, the voltage and current are measured between the reference electrode 220 and the ion selective electrodes 217 to 219 desired to be measured. The direct-current resistance R is expressed by $R=I_r/V_r$, where $V_r$ is the voltage and $I_r$ is the current. However, in reality, the ion selective electrode has a voltage $E_{1,n}$ caused by the ion selective electrode itself as illustrated in FIG. 9, as well as the resistance r. Thus, R and r are not necessarily equal, and $r=(V_r-E_{1,n})/I_r$. Accordingly, an accurate resistance value is determined by incorporating such correction (S805). The correction process may be performed by the resistance measuring unit 701 or by the operating and recording unit 203.

Finally, the calculated resistance value is output by the output unit 204 in the form of a screen output, printed characters and the like (S806). At this time, the operating and recording unit 203 may make an electrode replacement determination in accordance with the calculated resistance value, and output an electrode replacement-prompting display to the output unit 204 as needed. In this way, the user can be prompted to replace an electrode.

The operating and recording unit 203 may determine the state of the ion selective electrode in view of a potential response to the electrolyte (so-called slope sensitivity) in addition to the resistance value, so that the output unit 204 can output a more appropriate response.

Thus, in order to correctly measure the direct-current resistance value of the ion selective electrode, the voltage generated by the ion selective electrode itself must be measured. This step can be easily performed because an ion selective electrode for clinical examination normally has a sample solution with a known ion concentration.

According to the present embodiment, by measuring the direct-current resistance of the ion selective electrodes 217 to 219, the influence of parasitic capacity that has been the cause of resistance underestimation in alternating-current resistance measurement can be suppressed. By measuring the direct-current resistance between the reference electrode 220 and one of the ion selective electrodes 217 to 219, the direct-current resistance can be stably measured because of stable interface potential between the solution and the reference electrode 220 or the ion selective electrodes 217 to 219.

In addition, because the flow passageways of the electrodes 217 to 220 are filled with the solution in the dilution tank 211 using the sample solution suction nozzle 215 and the pump 222, the sample solution electrolyte concentration measurement and the resistance measurement for checking the ion selective electrode can be successively performed.

Second Embodiment

Figure 10:
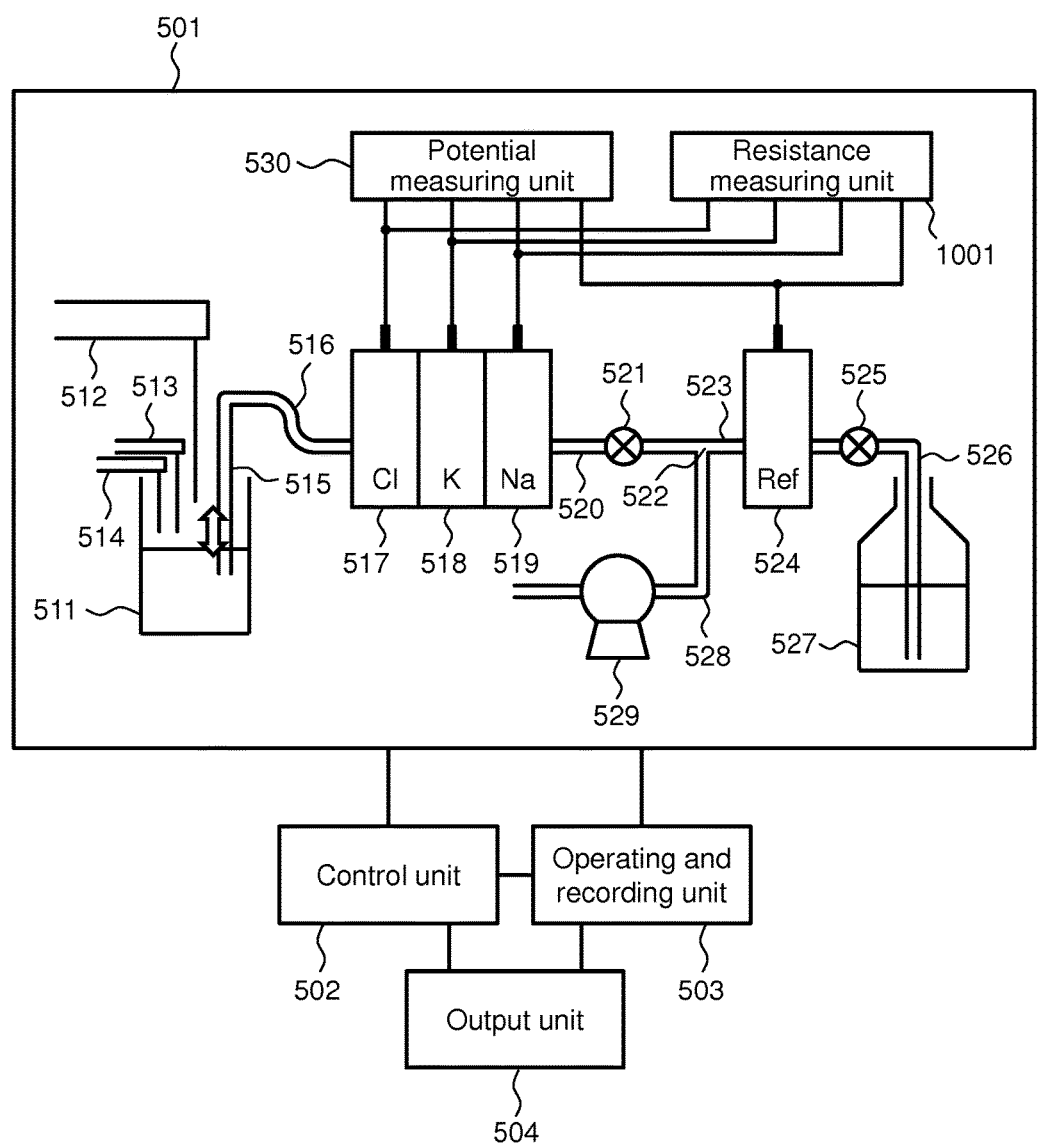
FIG. 10 is a schematic diagram of a second embodiment of the configuration for measuring the resistance value of the ion selective electrodes.

FIG. 10 is a schematic diagram of an example of the configuration for measuring the resistance value of the ion selective electrodes in the electrolyte concentration measuring apparatus of FIG. 5. Compared to the configuration of FIG. 5, a resistance measuring unit 1001 is added. The resistance measuring unit 1001 is electrically connected to the terminals of the ion selective electrodes 517 to 519 and the reference electrode 524.

Figure 11:
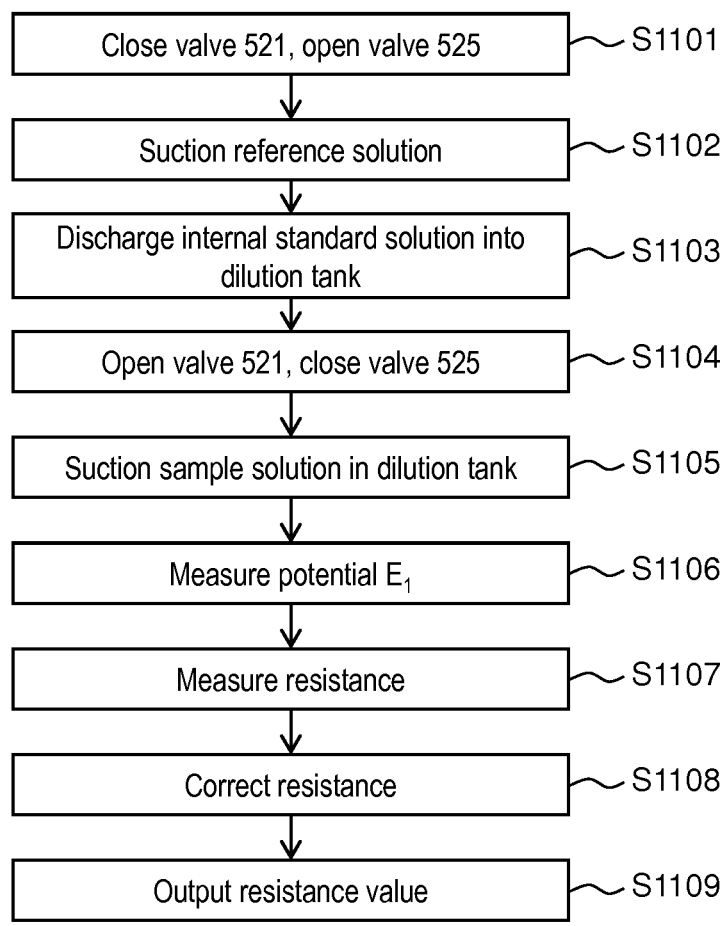
FIG. 11 shows an example of a flowchart of measurement of the resistance value of the ion selective electrodes.

FIG. 11 shows an example of a flowchart of measurement of the resistance value of the ion selective electrode using the electrolyte concentration measuring apparatus of FIG. 10. The process of FIG. 11 is mainly controlled by the control unit 502.

First, a valve 521 is closed and a valve 525 is opened (S1101), and a reference solution 527 is suctioned using a pump 529 and a piping 526 (S1102). As a result, the flow passageway of the reference electrode 524, a piping 523, and a junction 522 are filled with the reference solution.

Next, the internal standard solution is discharged into the dilution tank 511 using an internal standard solution dispensing nozzle 514 (S1103). Then the valve 521 is opened and the valve 525 is closed (S1104), and the internal standard solution in the dilution tank 511 is suctioned using the sample solution suction nozzle 515 and the pump 529 (S1105). As a result, the flow passageways of the electrodes 517 to 519, the piping 520, and the junction 522 are filled with the internal standard solution. At this time, because the ion selective electrodes 517 to 519 and the reference electrode 524 are connected by the pipings 520 and 523 and the junction 522 which are filled with the solution, the potential $E_{1,n}$ of the ion selective electrodes 517 to 519 with reference to the reference electrode 524 is measured using the potential measuring unit 530 (S1106).

Figure 12:
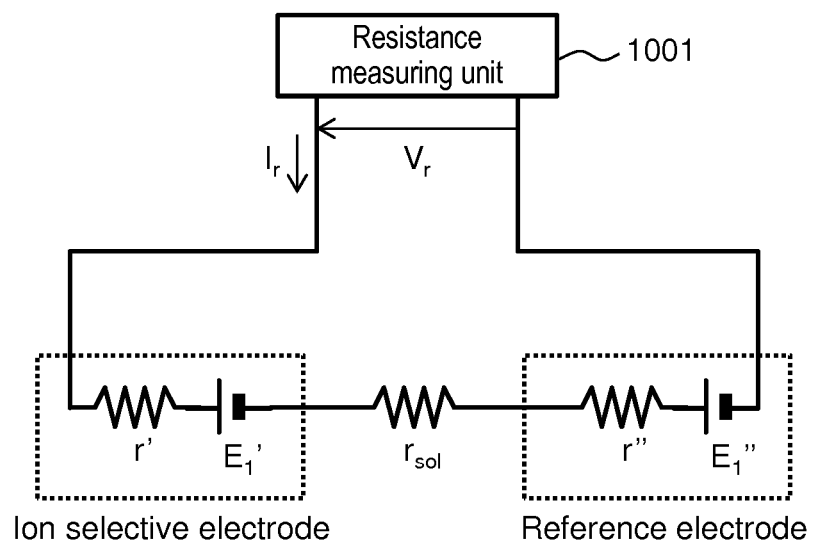
FIG. 12 shows an example of an equivalent circuit for the measurement of the resistance value of the ion selective electrode according to the second embodiment.

Then, using the resistance measuring unit 1101, the resistance value between the terminal of the reference electrode 524 and each terminal of the ion selective electrodes 517 to 519 is measured (S1107). The voltage and current between the reference electrode 524 and the ion selective electrodes 517 to 519 desired to be measured are measured. The equivalent circuit is illustrated in FIG. 12, where the measurement results are the voltage $V_r$ and the current $I_r$. In the equivalent circuit, where r' is the resistance of the ion selective electrode and $E_1'$ is its electromotive force, r" is the resistance of the reference electrode and $E_1''$ is its electromotive force, and $r_{sol}$ is the solution resistance in piping, the following expression holds:

$$r' + r'' + r_{sol} = \frac{V_r - (E_1' + E_1'')}{I_r} = \frac{V_r - E_{1,n}}{I_r} \quad \text{[Expression 3]}$$

Normally, the reference electrode resistance r" and the solution resistance $r_{sol}$ are sufficiently small compared with the resistance r' of the ion selective electrode to be measured, so there would be no problem if $r' \approx r'+r''+r_{sol}$. However, in the configuration of FIG. 10, the solution resistance $r_{sol}$ cannot be disregarded due to the piping 520 and the piping 523. An actual measurement showed that the solution resistance was 2 MΩ relative to the resistance value 8 MΩ of the ion selective electrode. In addition, when an ion selective electrode is used for the reference electrode 524, r″ may also have a value that cannot be disregarded relative to r′. In any case, after the resistance value measurement, correction is made by performing computation according to the above expression (S1108). The correction process may be performed by the resistance measuring unit 1001, or by the operating and recording unit 503.

Finally, the calculated resistance value is output by the output unit 504 in the form of a screen output, printed characters and the like (S1109). At this time, the operating and recording unit 503 may make an electrode replacement determination in accordance with the calculated resistance value, and output a display to the output unit 504 prompting electrode replacement as needed. In this way, the user can be prompted to replace an electrode.

The piping 520 and the piping 523, which may not necessarily be the best for resistance measurement, are effective in increasing the accuracy of electrolyte concentration measurement. This is because during normal operation, the reference electrode 524 does not come into contact with the solution including the specimen, and the reference solution 527 is replaced for each measurement, and therefore the potential of the reference electrode 524 can be readily stabilized.

According to the present embodiment, in the configuration in which the solution in the dilution tank 511 is introduced into the flow passageways of the ion selective electrodes 517 to 519, and in which the reference solution 527 is introduced into the flow passageway of the reference electrode 524, by measuring the direct-current resistance of the ion selective electrodes 517 to 519, the influence of parasitic capacity that has been the cause of resistance underestimation in alternating-current resistance measurement can be suppressed.

The present embodiment is also provided with the means for introducing the solution in the dilution tank 511 into the flow passageways of the ion selective electrodes 517 to 519, and for introducing the reference solution 527 into the flow passageway of the reference electrode 524. Accordingly, the sample solution electrolyte concentration measurement and the resistance measurement for checking the ion selective electrode can be successively performed.

Third Embodiment

Figure 13:
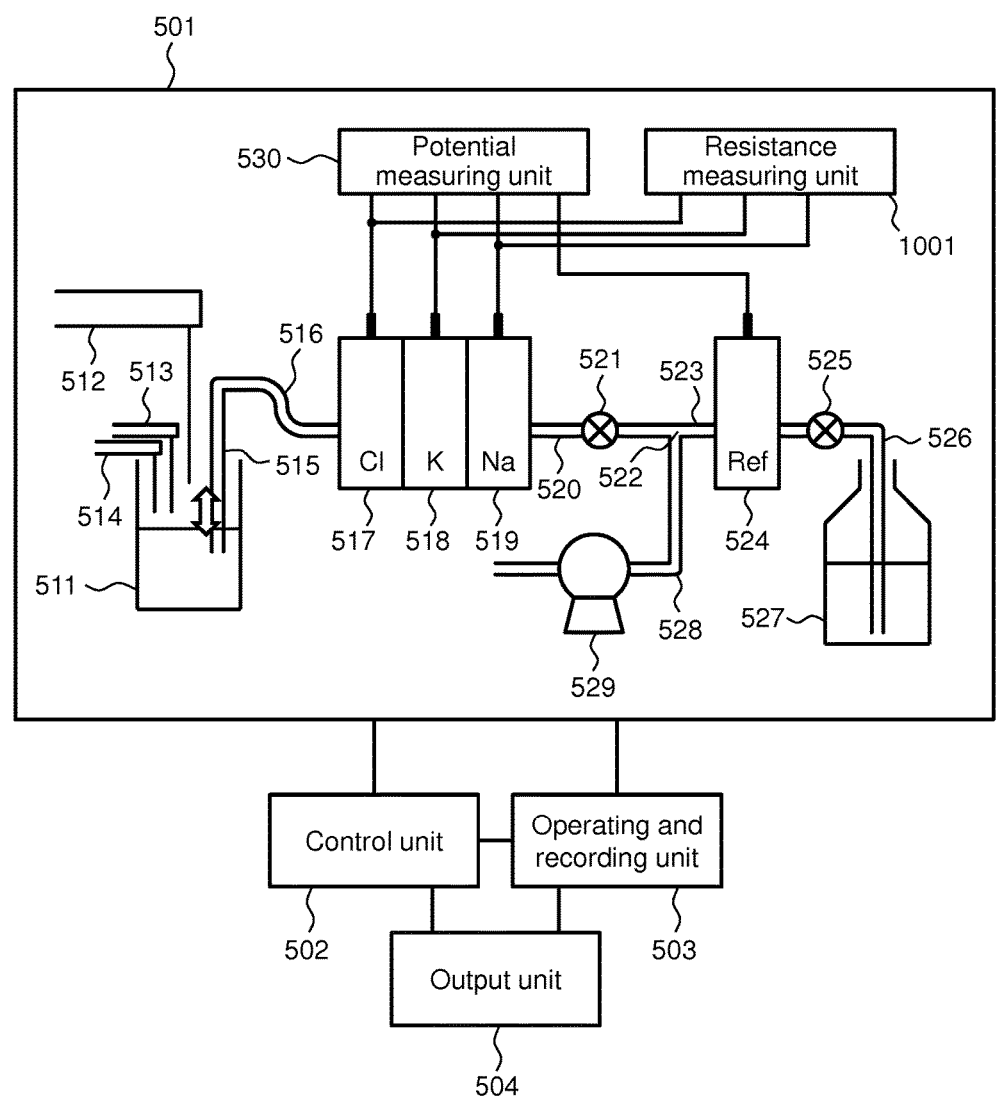
FIG. 13 is a schematic diagram of a third embodiment of the configuration for measuring the resistance value of the ion selective electrodes.

FIG. 13 is a schematic diagram of another example of the configuration for measuring the resistance value of the ion selective electrodes in the electrolyte concentration measuring apparatus of FIG. 5. The present embodiment is an example of a configuration in which an improvement is made to suppress the influence of solution resistance. Compared to the configuration of FIG. 5, the resistance measuring unit 1001 is added. The resistance measuring unit 1001 is electrically connected to the terminals of the electrodes 517 to 519.

As a feature of the present embodiment, an ion selective electrode with a relatively small resistance is used instead of the reference electrode 524, which is subject to the influence of solution resistance at the time of resistance measurement. In the present example, the ion selective electrode corresponds to the chlorine ion selective electrode 517. Compared with the resistance, normally on the order of 8 MΩ, of the potassium ion selective electrode 518 or the sodium ion selective electrode 519 including vinyl chloride and plasticizer as principal components, the resistance value of the chlorine ion selective electrode 517 based on an ion-exchange membrane was several orders of magnitude smaller at 10 KΩ.

While in the present example, the chlorine ion selective electrode 517 is used as a reference electrode during resistance measurement, other ion selective electrodes may be used. For example, as the reference electrode for resistance measurement, an ion selective electrode having a lower resistance than the solution resistance of the piping 520 and the piping 523 may be used. As described above, the ion selective electrode based on an ion-exchange membrane tends to have a relatively small resistance. Accordingly, an ion selective electrode based on an ion-exchange membrane may be used as the reference electrode at the time of resistance measurement.

In the present example, the measurement of direct-current resistance includes: measuring the electromotive force between the plurality of ion selective electrodes 517 to 519 and the reference electrode 524; measuring the voltage and current between two of the plurality of ion selective electrodes 517 to 519; and determining the sum of the resistance values of the two ion selective electrodes from the electromotive force, the voltage, and the current. The details will be described below.

Figure 14:
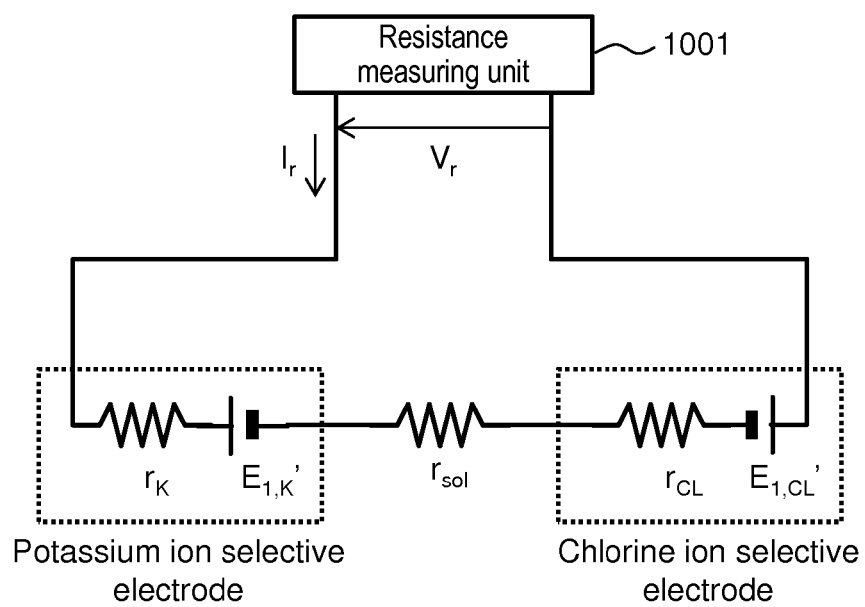
FIG. 14 shows an example of an equivalent circuit for the measurement of the resistance value of the ion selective electrode according to the third embodiment.

FIG. 14 shows an example of the equivalent circuit for the measurement of the resistance value of the ion selective electrode according to the present embodiment. In the present example, resistance measurement between the chlorine ion selective electrode 517 and the potassium ion selective electrode 518 will be described. When the resistance of the potassium ion selective electrode 518 is $r_K$ and its electromotive force is $E_{1,K}'$, the resistance of the chlorine ion selective electrode 517 is $r_{CL}$ and its electromotive force is $E_{1,CL}'$, and the solution resistance is $r_{SOL}$, the relationship $E_{1,K} - E_{1,CL} = E_{1,K}' - E_{1,CL}'$ holds between the electromotive forces $E_{1,K}$ and $E_{1,CL}$ measured by the potential measuring unit 530 for the respective ion selective electrodes. The voltage and current between the ion selective electrodes 517 and 518 are measured, obtaining voltage $V_r$ and current $I_r$. With regard to resistance measurement, the following relationship expression holds, whereby the sum of the resistance values can be determined.

$$r_K + r_{CL} + r_{sol} = \frac{V_r - (E_{1,K}' - E_{1,CL}')}{I_r} = \frac{V_r - (E_{1,K} - E_{1,CL})}{I_r} \quad \text{[Expression 4]}$$

Because the chlorine ion selective electrode 517 and the potassium ion selective electrode 518 are adjacent to each other, the solution resistance is small, such as on the order of 0.2 MΩ. As a result, the measured resistance value is approximately equal to the resistance value of the potassium ion selective electrode 518. Thus, resistance measurement is performed using an ion selective electrode of which the resistance is known to be small, instead of the reference electrode 524. Then, correction is performed using the potential $E_{1,n}$ measured for each ion selective electrode, whereby a resistance value can be determined while suppressing the influence of solution resistance thereon. In this case, because the resistance value of the chlorine ion selective electrode 517 is sufficiently small compared with the potassium ion selective electrode 518, resistance measurement will not be affected much even if the resistance of the small chlorine ion selective electrode 517 is varied.

Thus, according to the present embodiment, in the configuration in which the reference electrode is spaced apart from and connected to the other ion selective electrodes via piping or a flow passageway, direct-current resistance is measured between the ion selective electrode using an ion-exchange membrane as a sensitive membrane (chlorine ion selective electrode), for example, and the electrode desired to be measured (such as the sodium ion selective electrode, the potassium ion selective electrode, the magnesium ion selective electrode, or the calcium ion selective electrode). Because the resistance value of an ion selective electrode is measured with reference to one of the ion selective electrodes instead of using a reference electrode, the influence of solution resistance between the ion selective electrode and the reference electrode can be suppressed. Accordingly, the resistance value of the ion selective electrode can be measured with higher accuracy.

Fourth Embodiment

Figure 15:
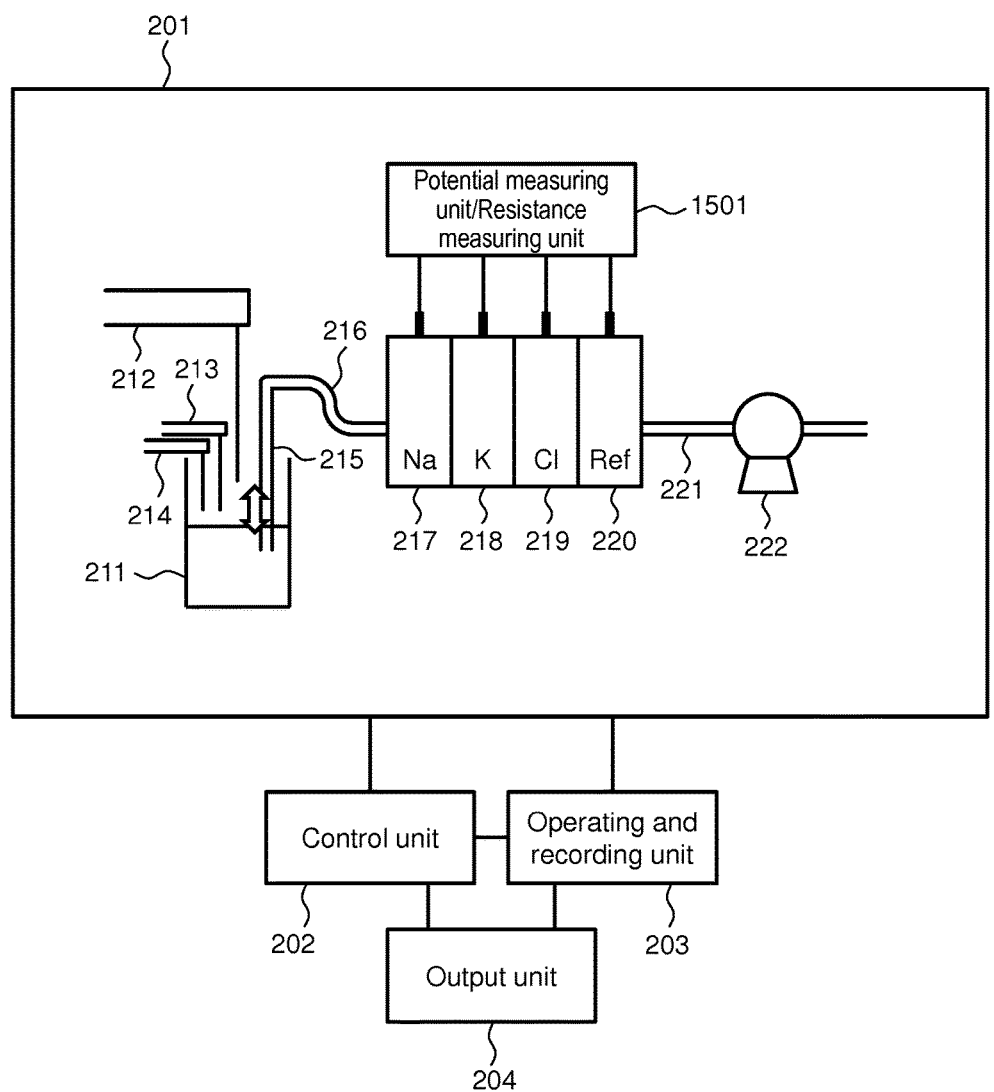
FIG. 15 is a schematic diagram of a fourth embodiment of the configuration for measuring the resistance value of the ion selective electrodes.

FIG. 15 is a schematic diagram of another example of the configuration for measuring the resistance value of the ion selective electrode in the electrolyte concentration measuring apparatus of the FIG. 2. In the present embodiment, the potential measuring unit 223 is replaced with a potential measuring unit/resistance measuring unit 1501. Namely, the potential measuring unit/resistance measuring unit 1501 serves for both potential measurement and resistance measurement. The potential measuring unit/resistance measuring unit 1501 is electrically connected to the terminals of the electrodes 217 to 220.

Figure 16:
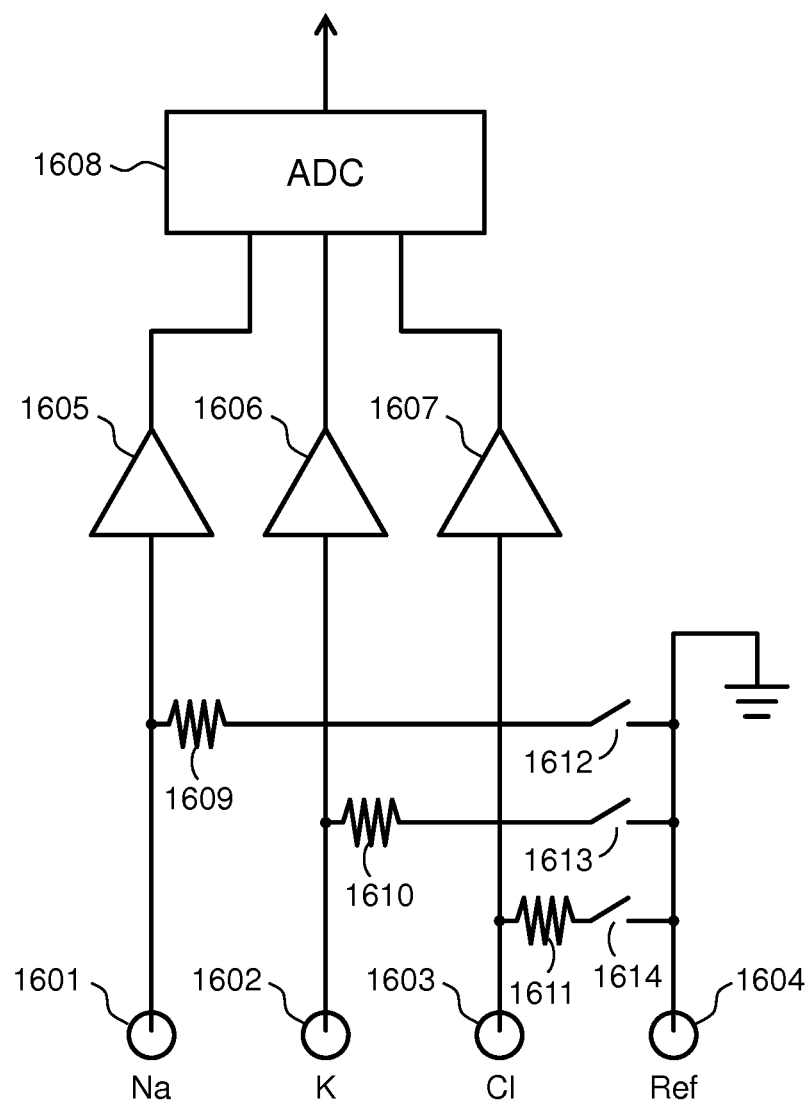
FIG. 16 is a schematic diagram of an example of a potential measuring unit/resistance measuring unit.

FIG. 16 is a circuit diagram of an example of the potential measuring unit/resistance measuring unit 1501. A terminal 1604 to which the reference electrode 220 is connected is connected to ground. Terminals 1601 to 1603 to which the other electrodes 217, 218, and 219 are connected are connected to amplifiers 1605 to 1607 with an input impedance on the order of 1 GΩ.

Outputs from the amplifiers 1605 to 1607 are input to an analog-digital converter (AD converter) 1608, and the AD converter 1608 outputs a digital value. Between the terminal 1604 and the terminals 1601 to 1603, resistors 1609 to 1611 and switches (switch units) 1612 to 1614 are connected.

In the present example, the direct-current resistance measurement includes: measuring a first electromotive force ($E_{1, n, OPEN}$ as will be described below) between at least one of the plurality of ion selective electrodes 217 to 219 and the reference electrode 220; measuring a second electromotive force ($E_{1, n, CLOSE}$ as will be described below) between at least the one of the ion selective electrodes 217 to 219 and the reference electrode 220 with the at least one of the ion selective electrodes 217 to 219 and the reference electrode 220 being connected by the resistors 1609 to 1611 with known resistance values; and determining a direct-current resistance from the first electromotive force, the second electromotive force, and the resistance values of the resistors 1609 to 1611. The details will be described below.

Figure 17:
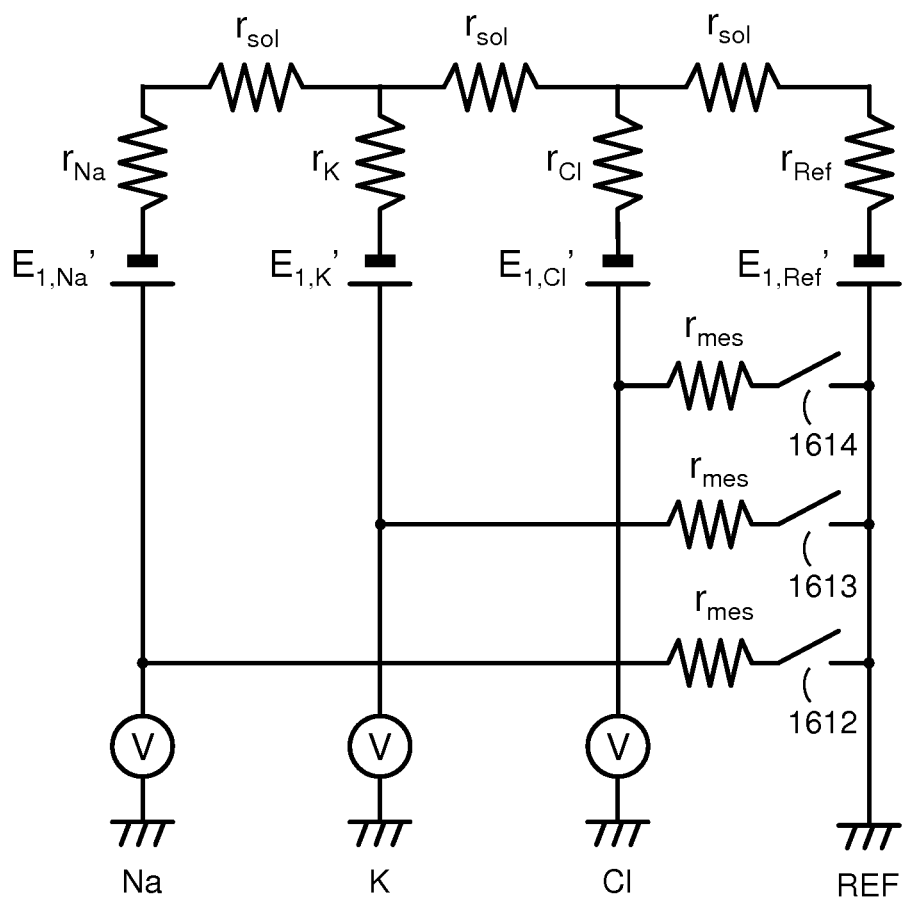
FIG. 17 shows an equivalent circuit for describing the operating principle of the circuit diagram of FIG. 16.

FIG. 17 shows an equivalent circuit for describing the operating principle of the circuit diagram of FIG. 16. The voltage $E_{1, n, OPEN}$ (n is the respective ion species) measured with the switches 1612 to 1614 open is as follows.

$$E_{1,n,OPEN} = E'_{1,n} - E'_{1,Ref}$$ [Expression 5]

On the other hand, the voltage $E_{1, Na, CLOSE}$ measured with the switch 1612 closed, for example, is as follows.

$$E_{1,Na,CLOSE} = (E'_{Na,n} - E'_{1,Ref}) \frac{r_{mes}}{r_{Na} + 3r_{sol} + r_{Ref} + r_{mes}} =$$ [Expression 6]

$$E_{1,Na,OPEN} \frac{r_{mes}}{r_{Na} + 3r_{sol} + r_{Ref} + r_{mes}}$$

Solving the equation yields the following.

$$r_{Na} + 3r_{sol} + r_{Ref} = \left(\frac{E_{1,Na,OPEN}}{E_{1,Na,CLOSE}} - 1\right) r_{mes}$$ [Expression 7]

$$r_{Na} \cong r_{Na} + 3r_{sol} + r_{Ref}$$ [Expression 8]

Accordingly, by comparing the voltage measured with the switch open with the voltage measured with the switch closed, the resistance value of the ion selective electrode can be determined.

Figure 18:
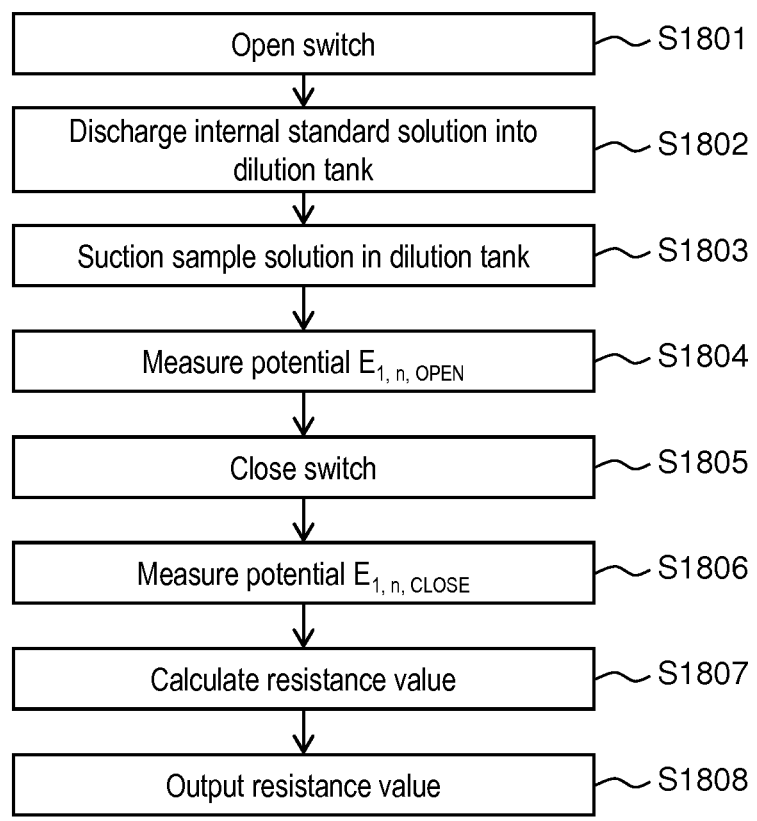
FIG. 18 shows an example of a flowchart of measurement of the resistance value of the ion selective electrode.

FIG. 18 shows an example of a flowchart of measurement of the resistance value of the ion selective electrode using the electrolyte concentration measuring apparatus of FIG. 15. The process of FIG. 18 is mainly controlled by the control unit 502.

First, the switches 1612 to 1614 are opened (S1801). Then, using the internal standard solution dispensing nozzle 214, the internal standard solution is discharged into the dilution tank 211 (S1802).

Next, using the sample solution suction nozzle 215 and the pump 222, the internal standard solution in the dilution tank 211 is suctioned (S1803), whereby the flow passageways of the electrodes 217 to 220 are filled with the internal standard solution. Then, using the potential measuring unit/resistance measuring unit 1501, the potentials of the ion selective electrodes 217 to 219 with reference to the reference electrode 220 are measured (S1804). Herein, the potentials of the electrodes 217 to 219 with the switches 1612 to 1614 open are $E_{1, n, OPEN}$ (n is the respective ion species).

The switches 1612 to 1614 are then closed (S1805). Then, using the potential measuring unit/resistance measuring unit 1501, the potentials of the electrodes 217 to 219 with reference to the reference electrode 220 are measured (S1806). Herein, the potentials of the electrodes 217 to 219 with the switches 1612 to 1614 closed are $E_{1, n, CLOSE}$.

Then, from $E_{1, n, OPEN}$, $E_{1, n, CLOSE}$, and the resistance values of the resistors 1609 to 1611, the resistance values of the ion selective electrodes 217, 218, and 219 are calculated (S1807). The calculation process may be performed by the potential measuring unit/resistance measuring unit 1501, or by the operating and recording unit 203.

Finally, the calculated resistance values are output by the output unit 204 in the form of a screen output, printed characters and the like (S1808). At this time, the operating and recording unit 203 may make an electrode replacement determination in accordance with the calculated resistance values, and output a display prompting electrode replacement to the output unit 204 as needed. In this way, the user can be prompted to replace an electrode.

Preferably, the potential measurement with the switches 1612 to 1614 closed is performed by closing the switches one by one and measuring the potential one after another from the viewpoint of the equivalent circuit. However, in reality, because the solution resistance and the resistance of the reference electrode 220 are small compared with the resistance of the ion selective electrodes 217, 218, and 219 or the resistance values of the resistors 1609 to 1611, closing the switches 1612 to 1614 simultaneously would not have much influence.

Figure 19:
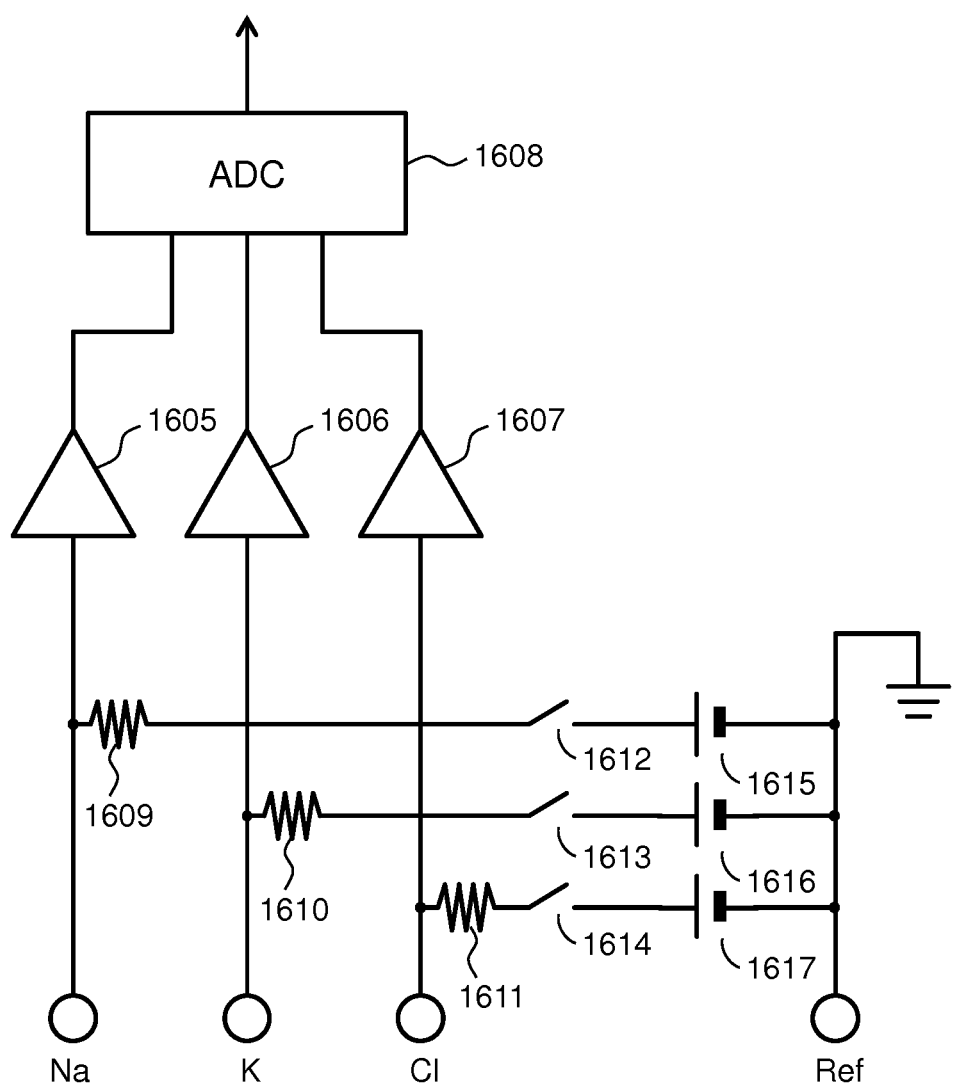
FIG. 19 is a schematic diagram of an example of the potential measuring unit/resistance measuring unit.

For an accurate resistance value measurement, it is also preferable that the potential $E_{1, n, OPEN}$ with the switches 1612 to 1614 open is not around 0 V. This point is desirably considered when adjusting the respective ion concentration of the internal standard solution used for resistance measurement. FIG. 19 is a circuit diagram of another example of the potential measuring unit/resistance measuring unit 1501. As illustrated in FIG. 19, direct-current power supplies 1615, 1616, and 1617 may be added in series with the resistors 1609, 1610, and 1611 and the switches 1612, 1613, and 1614 as needed.

According to the present embodiment, the electromotive forces are measured when the ion selective electrode of which the resistance is to be measured is connected via a resistor with a known resistance value and when disconnected, and the resistance value of the ion selective electrode is determined from the electromotive forces. The configuration enables the voltmeter used for electrolyte concentration measurement and the voltmeter used for resistance measurement to be shared and commonly provided by a single unit for potential measurement and resistance measurement (potential measuring unit/resistance measuring unit 1501).

In addition to reducing cost and space, adverse effects on the electrolyte measurement can be minimized as is the original purpose. By sharing the voltmeters, resistance measurement reflecting the high accuracy of electrolyte measurement can be implemented.

Fifth Embodiment

Figure 20:
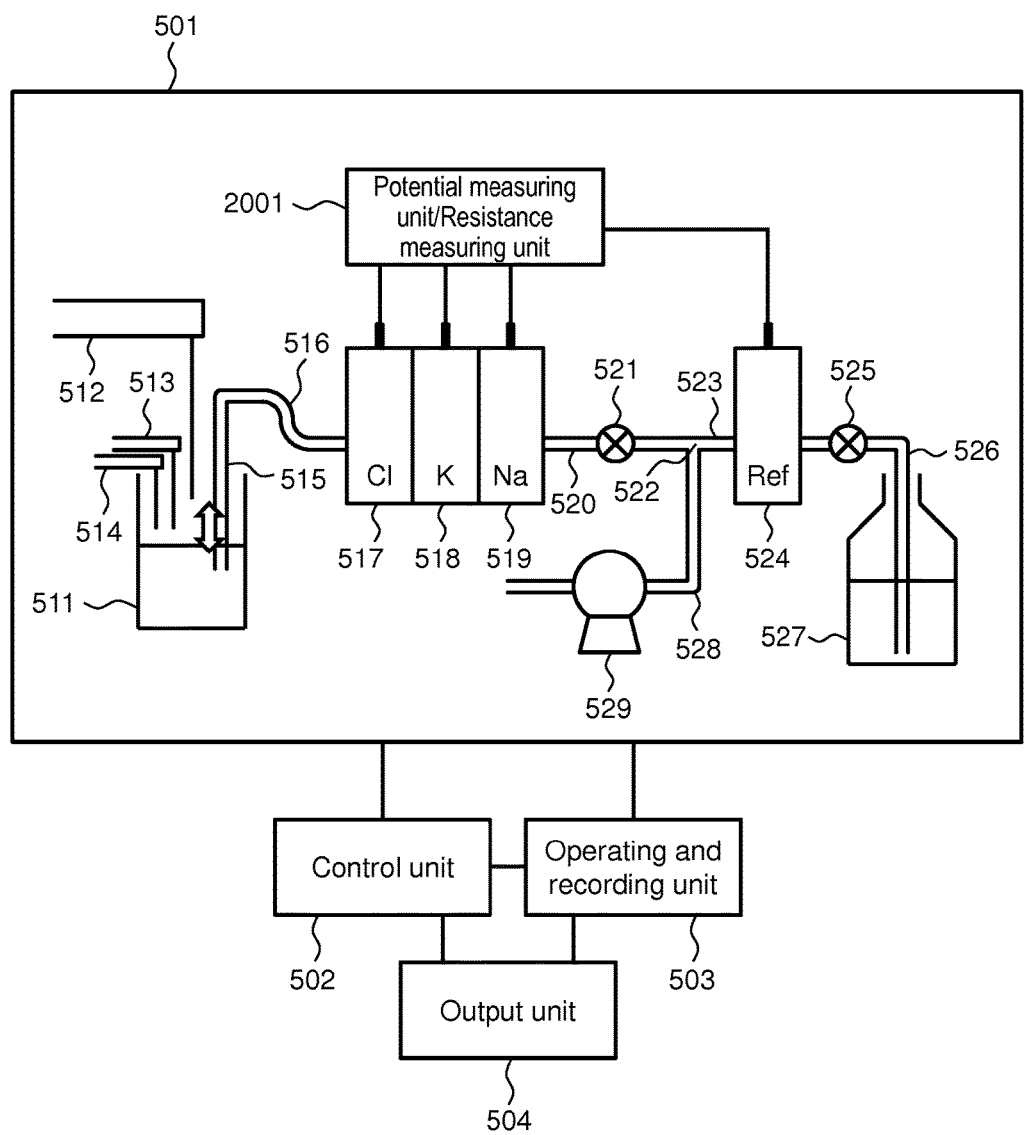
FIG. 20 is a schematic diagram of a fifth embodiment of the configuration for measuring the resistance value of the ion selective electrodes.

FIG. 20 is a schematic diagram of another example of the configuration for measuring the resistance value of the ion selective electrodes in the electrolyte concentration measuring apparatus of FIG. 5. According to the present embodiment, the potential measuring unit 530 is replaced by a potential measuring unit/resistance measuring unit 2001. Namely, the potential measuring unit/resistance measuring unit 2001 performs both potential measurement and resistance measurement. The potential measuring unit/resistance measuring unit 2001 is electrically connected to the terminals of the ion selective electrodes 517 to 519 and the terminal of the reference electrode 524.

Figure 21:
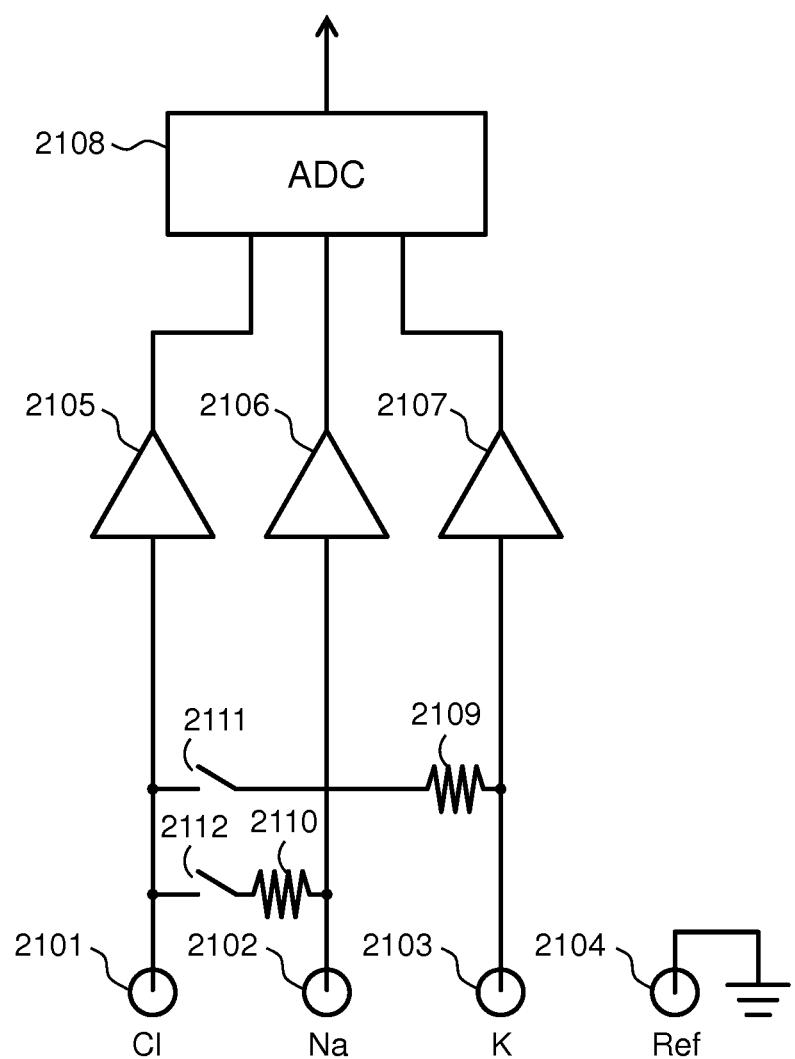
FIG. 21 is a schematic diagram of an example of the potential measuring unit/resistance measuring unit.

For the potential measuring unit/resistance measuring unit 2001, the circuit diagram shown in FIG. 16 or FIG. 19 may be used, or the circuit diagram of FIG. 21 may be used. FIG. 21 is a circuit diagram of an example of the potential measuring unit/resistance measuring unit 2001.

A terminal 2104 to which the reference electrode 524 is connected is connected to ground. Terminals 2101 to 2103 to which the other electrodes 517, 518, and 519 are connected are connected to amplifiers 2105 to 2107 with an input impedance on the order of 1 GΩ. Outputs from the amplifier 2105 to 2107 are input to an analog-digital converter (AD converter) 2108, and the AD converter 2108 outputs a digital value. Between the terminal 2101 and the terminals 2102 and 2103 respectively, resistors 2109 and 2110 and switches (switch units) 2111 and 2112 are connected.

In the present example, the direct-current resistance measurement includes: measuring a first electromotive force ($E_{1, n, OPEN}$ as will be described below) between a first ion selective electrode among the plurality of ion selective electrodes 517 to 519 and the reference electrode 524; measuring a second electromotive force ($E_{1, n, OPEN}$ as will be described below) between a second ion selective electrode among the plurality of ion selective electrodes 517 to 519 and the reference electrode 524; measuring a third electromotive force ($E_{1, n, CLOSE}$ as will be described below) between the first ion selective electrode and the reference electrode 524 and a fourth electromotive force ($E_{1, n, CLOSE}$ as will be described below) between the second ion selective electrode and the reference electrode 524, with the first ion selective electrode and the second ion selective electrode being connected by resistors 2109 and 2110 with known resistance values; and determining a resistance value of the first ion selective electrode and a resistance value of the second ion selective electrode from the first through fourth electromotive forces and the resistance values of the resistors 2109 and 2110. In the following description, the first ion selective electrode corresponds to the chlorine ion selective electrode 517, and the second ion selective electrode corresponds to the potassium ion selective electrode 518 by way of example.

Figure 22:
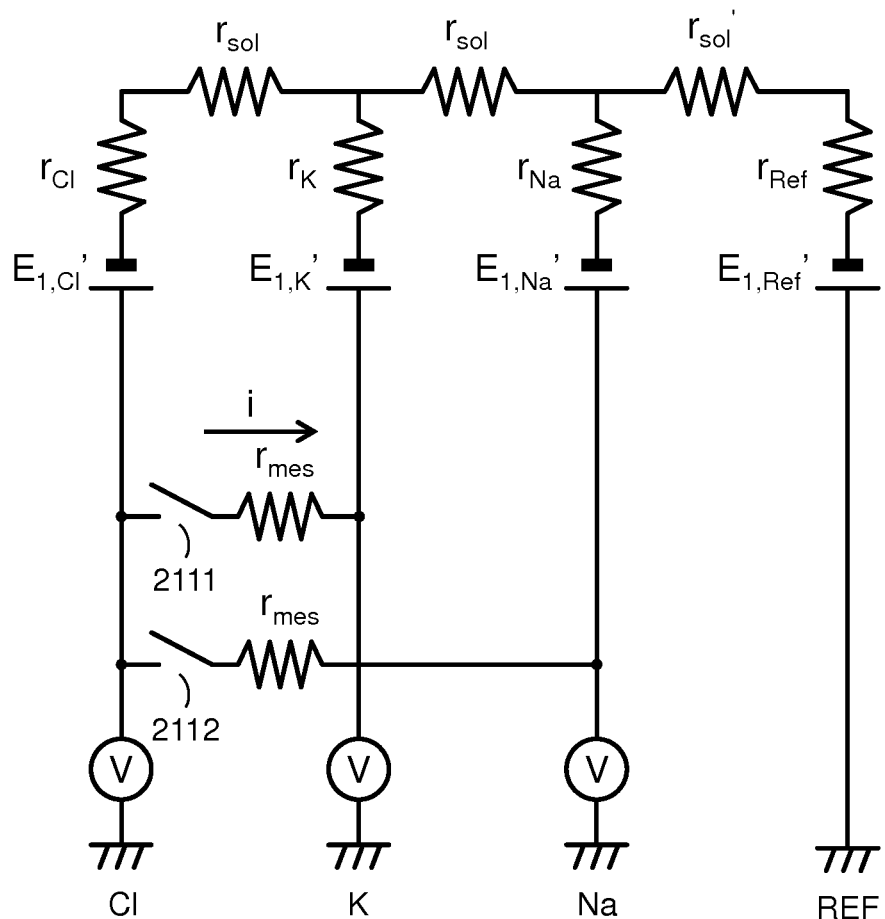
FIG. 22 shows an equivalent circuit for describing the operating principle of the circuit diagram of FIG. 21.

FIG. 22 shows an equivalent circuit for describing the operating principle of the circuit diagram of FIG. 21. The solution resistance $r_{sol}'$ is greater than the other solution resistances $r_{sol}$ due to the influence of the piping 520 and the piping 523. The voltage $E_{1, n, OPEN}$ (n is the respective ion species) measured with the switches 2111 to 2112 open is as follows.

$$E_{1,n,OPEN} = E_{1,n}' - E_{1,Ref}' \quad \text{[Expression 9]}$$

A current i that flows through the resistors as the switch 2111 is closed is as follows.

$$i = \frac{E_{1,Cl}' - E_{1,K}'}{r_{Cl} + r_K + r_{sol} + r_{mes}} \quad \text{[Expression 10]}$$

Accordingly, the voltages $E_{1, Cl, CLOSE}$ and $E_{1, K, CLOSE}$ that are measured with the switch 2111 closed are as follows.

$$E_{1,Cl,CLOSE} = E_{1,Cl}' - E_{1,Ref}' - i(r_{Cl} + r_{sol}) = E_{1,Cl,OPEN} - i$$
$$(r_{Cl} + r_{sol}) E_{1,K,CLOSE} = E_{1,K}' - E_{1,Ref}' + ir_K = $$
$$E_{1,K,OPEN} + ir_K \quad \text{[Expression 11]}$$

Solving the above yields the following.

$$r_{Cl} + r_K + r_{sol} = \left( \frac{E_{1,Cl,OPEN} - E_{1,K,OPEN}}{E_{1,Cl,CLOSE} - E_{1,K,CLOSE}} - 1 \right) r_{mes} \quad \text{[Expression 12]}$$

$$r_{Cl} + r_{sol} = \frac{E_{1,Cl,CLOSE} - E_{1,Cl,OPEN}}{E_{1,K,CLOSE} - E_{1,K,OPEN}} r_K$$

Accordingly, we have the following.

$$r_{Cl} \cong r_{Cl} + r_{sol} = \frac{E_{1,Cl,CLOSE} - E_{1,Cl,OPEN}}{E_{1,Cl,CLOSE} - E_{1,K,CLOSE}} r_{mes} \quad \text{[Expression 13]}$$

In this way, the resistance values of the ion selective electrodes 517, 518, and 519 can be determined. As is clear from the above expression, resistance measurement can be performed without being affected by the influence of the large solution resistance $r_{sol}'$.

Because the resistance values of the two ion selective electrodes connected by a switch and a resistor can be separately calculated, it is not necessary that one of the two ion selective electrodes has a lower resistance. In practice, it is preferable to select an anion selective electrode, such as the chlorine ion selective electrode 517, and a cation selective electrode, such as the potassium ion selective electrode 518, and to connect them by a switch and a resistor, as in the example. This is because the anion selective electrode and the cation selective electrode respond in opposite ways with respect to a change in ion concentration, so that the potential difference between the ion selective electrodes ($E_{1, Cl, CLOSE} - E_{1, K, CLOSE}$ as described above) can be readily increased and therefore more accurate resistance measurement can be performed.

Figure 23:
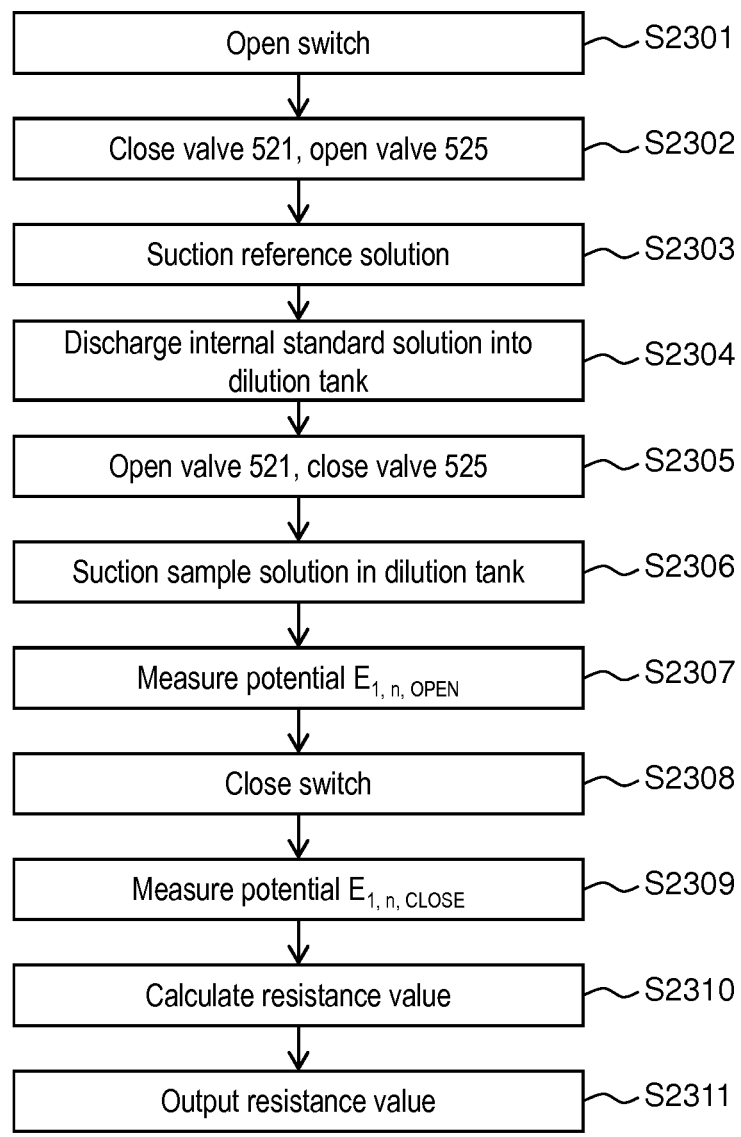
FIG. 23 shows an example of a flowchart of measurement of the resistance value of the ion selective electrode.

FIG. 23 shows an example of a flowchart of measurement of the resistance value of the ion selective electrode using the electrolyte concentration measuring apparatus of FIG. 20. The process of FIG. 23 is mainly controlled by the control unit 502.

First, the switches 2111 and 2112 are opened (S2301), and the valve 521 is closed while the valve 525 is opened (S2302). Then, using the pump 529, the reference solution 527 is suctioned (S2303). In this way, the flow passageway of the reference electrode 524, the piping 523, and the junction 522 are filled with the reference solution.

Then, using the internal standard solution dispensing nozzle 514, the internal standard solution is discharged into the dilution tank 511 (S2304). The valve 521 is then opened and the valve 525 is closed (S2305), and the internal standard solution in the dilution tank 511 is suctioned using the sample solution suction nozzle 515 and the pump 529 (S2306). In this way, the flow passageways of the ion selective electrodes 517 to 519, the piping 520, and the junction 522 are filled with the internal standard solution. At this time, because the ion selective electrodes 517 to 519 and the reference electrode 524 are connected by the pipings 520 and 523 and the junction 522 which are filled with the solution, the potentials of the ion selective electrodes 517 to 519 with reference to the reference electrode 524 are measured using the potential measuring unit/resistance measuring unit 2001 (S2307). Herein, the potentials of the ion selective electrodes 517 to 519 with the switches 2111 and 2112 opened are $E_{1, n, OPEN}$ (n is the respective ion species).

Then, the switches 2111 and 2112 are closed (S2308), and the potentials of the ion selective electrodes 517 to 519 with reference to the reference electrode 524 are measured using the potential measuring unit/resistance measuring unit 2001 (S2309). Herein, the potentials of the ion selective electrodes 517 to 519 with the switches 2111 and 2112 closed are $E_{1, n, CLOSE}$.

Next, the resistance values of the ion selective electrodes 517, 518, and 519 are calculated from $E_{1, n, OPEN}$, $E_{1, n, CLOSE}$, and the resistance values of the resistors 2109 and 2110 (S2310). The calculation process may be performed by the potential measuring unit/resistance measuring unit 2001, or by the operating and recording unit 503.

Finally, the calculated resistance values are output by the output unit 504 in the form of a screen output, printed characters and the like (S2311). At this time, the operating and recording unit 503 may make an electrode replacement determination in accordance with the calculated resistance values of the electrodes, and output a display prompting electrode replacement to the output unit 504 as needed. In this way, the user can be prompted to replace an electrode.

Preferably, the potential measurement with the switches 2111 and 2112 closed is performed by closing the switches one by one and measuring one potential after another from the viewpoint of the equivalent circuit. However, in practice, the solution resistance is small compared with the resistance of the ion selective electrodes and the resistance values of the resistors 2109 and 2110, so that closing the switches 2111 and 2112 simultaneously would not have much influence.

Figure 24:
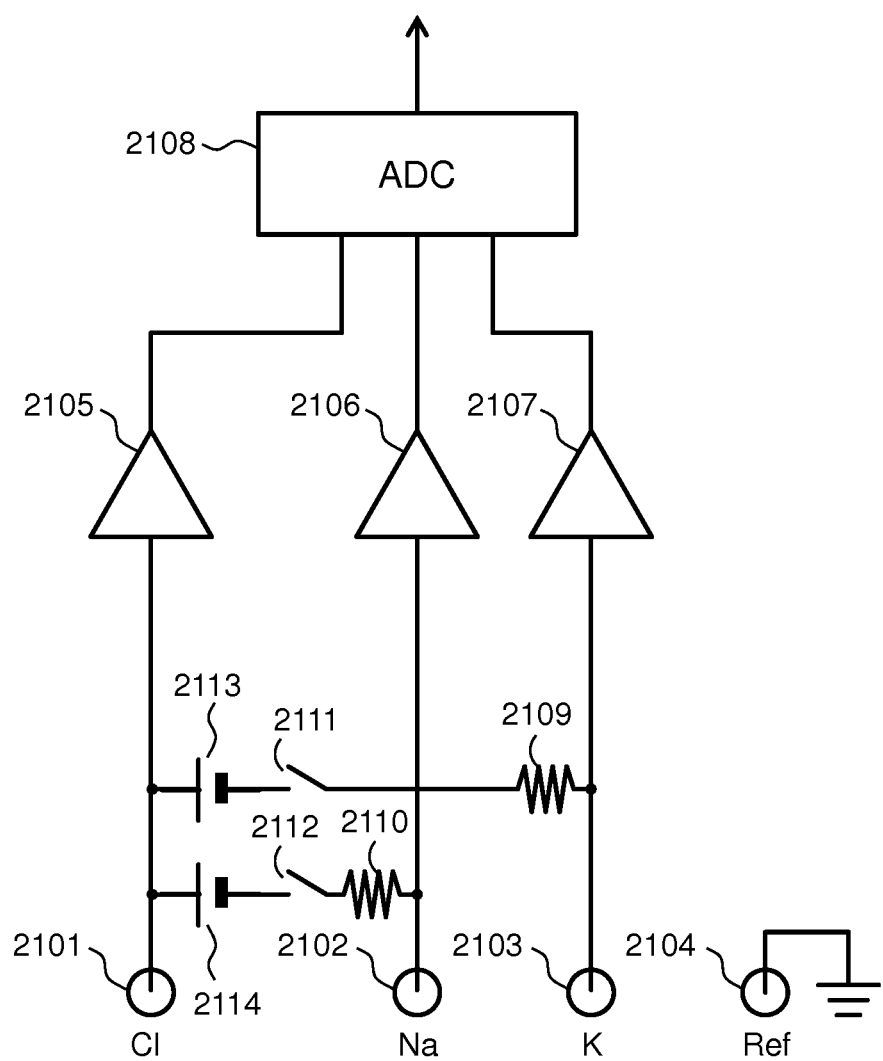
FIG. 24 is a schematic diagram of an example of the potential measuring unit/resistance measuring unit.

In order to measure the resistance values accurately, it is preferable that the potential $E_{1, n, OPEN}$ with the switches 2111 and 2112 open is not around 0 V. This point is desirably considered when adjusting the respective ion concentration of the internal standard solution used for resistance measurement. FIG. 24 is a circuit diagram of another example of the potential measuring unit/resistance measuring unit 2001. As illustrated in FIG. 24, direct-current power supplies 2113 and 2114 may be added in series with the resistors 2109 and 2110 and the switches 2111 and 2112, as needed.

According to the present embodiment, in the configuration in which the solution in the dilution tank 511 is introduced into the flow passageways of the ion selective electrodes 517 to 519, and in which the reference solution 527 is introduced into the flow passageway of the reference electrode 524, the electromotive forces are measured when the ion selective electrode of which the resistance is to be measured is connected via a resistor with a known resistance value and when disconnected, and the resistance value of the ion selective electrode is determined from the electromotive forces. The configuration enables the voltmeter used for electrolyte concentration measurement and the voltmeter used for resistance measurement to be shared and provided by a single unit for potential measurement and resistance measurement (potential measuring unit/resistance measuring unit 2001). Further, the resistance value of the ion selective electrode can be measured with higher accuracy without being affected by the influence of solution resistance between the ion selective electrodes 517 to 519 and the reference electrode 524.

Sixth Embodiment

Figure 25A:
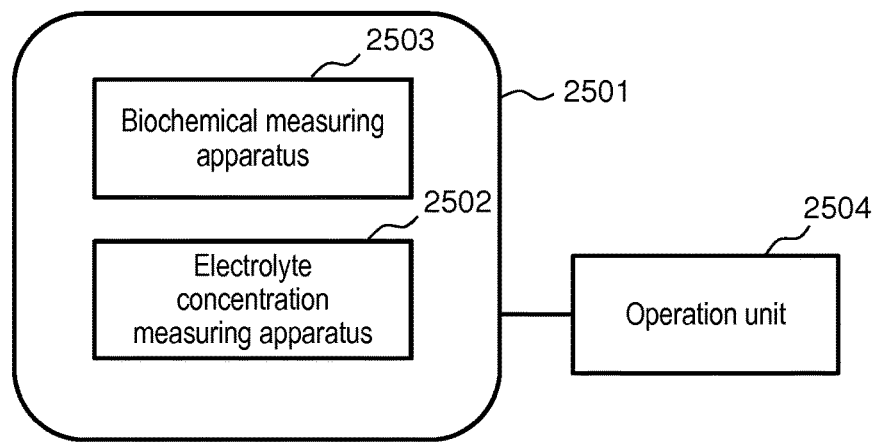
FIG. 25A shows an example of a system using the electrolyte concentration measuring apparatus.

FIG. 25A illustrates an example of a system using the electrolyte concentration measuring apparatus. The system of the present example is an automated clinical analyzer 2501. The automated clinical analyzer 2501 is provided with an electrolyte concentration measuring apparatus 2502 described above; a biochemical measuring apparatus 2503 that performs optical measurement; and an operation unit 2504 for operating the electrolyte concentration measuring apparatus 2502 and the biochemical measuring apparatus 2503. The operation unit 2504 includes an input unit, such as a keyboard and a pointing device, and an output unit such as a display. The automated clinical analyzer 2501 can be controlled by an operation from the operation unit 2504.

Figure 25B:
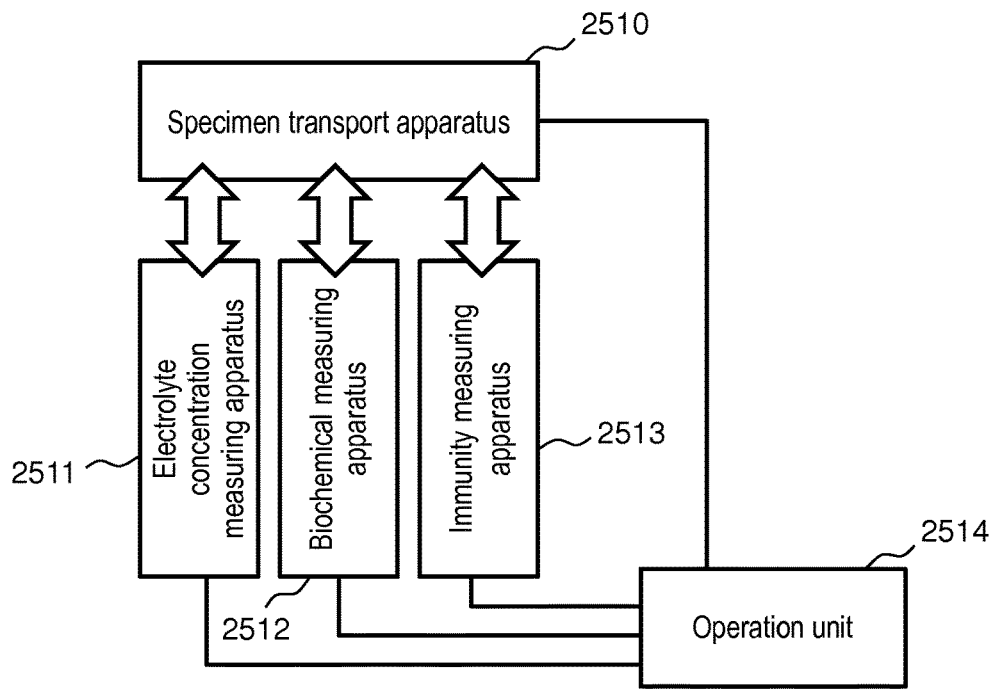
FIG. 25B shows an example of a system using the electrolyte concentration measuring apparatus.

FIG. 25B shows another example of the system using the electrolyte concentration measuring apparatus. The system of the present example is formed such that, as will be described below, various devices are independent from each other. The present system is provided with a specimen transport apparatus 2510; an electrolyte concentration measuring apparatus 2511 as described above; a biochemical measuring apparatus 2512 that performs optical measurement; an immunity measuring apparatus 2513 that measures a chemical component in sample by immune reaction; and an operation unit 2514. The apparatuses 2511, 2512, and 2513 exchange the specimen with the specimen transport apparatus 2510. The operation unit 2514 includes an input unit, such as a keyboard and a pointing device, and an output unit such as a display. In the present system, the apparatuses 2510, 2511, 2512, and 2513 can be controlled by an operation from the operation unit 2514.

The present invention is not limited to the above-described embodiments and may include various modifications. The embodiments have been described for facilitating an understanding of the present invention and are not necessarily limited to those provided with all of the configurations described. A part of the configuration of one embodiment may be replaced by the configuration of another embodiment, or the configuration of the other embodiment may be incorporated into the configuration of the one embodiment. With respect to a part of the configuration of each embodiment, addition of another configuration, deletion, or substitution may be made.

For example, all of the direct-current resistance measurements and computations may be performed by the resistance measuring unit 701 or 1001 or by the potential measuring unit/resistance measuring unit 1501 or 2001, or some of the computations may be handled by the operating and recording unit 203 or 503.

As described above, the control units 202 and 502 and the operating and recording units 203 and 503 may be implemented by software program codes for implementing the functions of the embodiments. In this case, an information processing apparatus may be provided with a storage medium having the program codes recorded therein, and the information processing apparatus (or CPU) may read the program codes stored in the storage medium. In this case, the program codes per se read from the storage medium will implement the functions of the embodiments, so that the program codes per se and the storage medium having the codes stored therein will constitute the present invention. Examples of the storage medium for supplying such program codes include flexible discs; CD-ROM; DVD-ROM; hard disks; optical disks; magneto-optical disks; CD-R; magnetic tapes; non-volatile memory cards; and ROM. The control units 202 and 502 and the operating and recording units 203 and 503 may be partly or entirely implemented by hardware by designing an integrated circuit, for example.

The control lines and information lines in the drawings are only those considered necessary for description purpose, and do not necessarily represent all of the control lines and information lines found in a product. All of the configurations may be mutually connected.

REFERENCE SIGNS LIST

101 Ion selective electrode cartridge
102 Flow passageway
103 Silver-silver chloride electrode
104 Internal solution
105 Sensitive membrane
201, 501 Measuring unit
202, 502 Control unit
203, 503 Operating and recording unit
204, 504 Output unit
211, 511 Dilution tank
212, 512 Specimen dispensing nozzle
213, 513 Diluting fluid dispensing nozzle
214, 514 Internal standard solution dispensing nozzle
215, 515 Sample solution suction nozzle
216, 221, 516, 520, 523, 526, 528 Piping
217, 519 Sodium ion selective electrode
218, 518 Potassium ion selective electrode
219, 517 Chlorine ion selective electrode
220, 524 Reference electrode
222, 529 Pump
223, 530 Potential measuring unit
301 to 304, 1601 to 1604, 2101 to 2104 Terminal
305 to 306, 1605 to 1607, 2105 to 2107 Amplifier
308, 1608, 2108 Analog-digital converter
521, 525 Valve
522 Junction
527 Reference solution
701, 1001 Resistance measuring unit
1501, 2001 Potential measuring unit/resistance measuring unit
1609 to 1611, 2109, 2110 Resistor
1612 to 1614, 2111, 2112 Switch
2501 Automated clinical analyzer

The invention claimed is:

1. An electrolyte concentration measuring apparatus comprising:
   a plurality of ion selective electrodes and one reference electrode;
   a sample introduction unit that introduces a sample solution into the plurality of ion selective electrodes and the reference electrode;
   a potential measuring unit that measures a voltage between the plurality of ion selective electrodes and the reference electrode; and
   a resistance measuring unit that measures a direct-current resistance of the plurality of ion selective electrodes, wherein the resistance measuring unit measures the direct-current resistance using two of the plurality of ion selective electrodes,
   and wherein the resistance measuring unit corrects the direct-current resistance using an electromotive force of the ion selective electrodes themselves.

2. The electrolyte concentration measuring apparatus according to claim 1, wherein the resistance measuring unit measures the direct-current resistance using one of the plurality of ion selective electrodes and the reference electrode.

3. The electrolyte concentration measuring apparatus according to claim 1, wherein one of the two of the plurality of ion selective electrodes is an ion selective electrode having a resistance lower than a solution resistance between the ion selective electrode and the reference electrode, or an ion selective electrode based on an ion-exchange membrane.

4. The electrolyte concentration measuring apparatus according to claim 1, wherein the resistance measuring unit measures the direct-current resistance using two of the plurality of ion selective electrodes and the reference electrode.

5. The electrolyte concentration measuring apparatus according to claim 1, further comprising a measuring unit that serves as both the potential measuring unit for voltage measurement and the resistance measuring unit for direct-current resistance measurement.

6. The electrolyte concentration measuring apparatus according to claim 5, wherein the resistance measuring unit includes:
   a resistor connected between one of the plurality of ion selective electrodes and the reference electrode; and
   a switch unit for connecting or disconnecting the resistance.

7. The electrolyte concentration measuring apparatus according to claim 5, wherein the resistance measuring unit includes:
   a resistor connected between two of the plurality of ion selective electrodes; and
   a switch unit for connecting or disconnecting the resistance.

8. The electrolyte concentration measuring apparatus according to claim 1, wherein:

the potential measuring unit measures an electromotive force between at least one of the plurality of ion selective electrodes and the reference electrode; and the resistance measuring unit measures a voltage and a current between the at least one of the ion selective electrodes and the reference electrode, and determines the direct-current resistance from the electromotive force, the voltage, and the current.

9. The electrolyte concentration measuring apparatus according to claim 1, wherein:

the potential measuring unit measures an electromotive force between at least one of the plurality of ion selective electrodes and the reference electrode; and the resistance measuring unit measures a voltage and a current between two of the plurality of ion selective electrodes, and determines a sum of resistance values of the two ion selective electrodes from the electromotive force, the voltage, and the current as the direct-current resistance.

10. The electrolyte concentration measuring apparatus according to claim 6, wherein:

the potential measuring unit measures a first electromotive force between at least one of the plurality of ion selective electrodes and the reference electrode;

the potential measuring unit measures a second electromotive force between the at least one ion selective electrode and the reference electrode with the at least one ion selective electrode and the reference electrode being connected by the resistor; and the resistance measuring unit determines the direct-current resistance from the first electromotive force, the second electromotive force, and a resistance value of the resistor.

11. The electrolyte concentration measuring apparatus according to claim 7, wherein:

the potential measuring unit measures a first electromotive force between a first ion selective electrode among the plurality of ion selective electrodes and the reference electrode, and a second electromotive force between a second ion selective electrode among the plurality of ion selective electrodes and the reference electrode;

the potential measuring unit measures, with the first ion selective electrode and the second ion selective electrode being connected by the resistor, a third electromotive force between the first ion selective electrode and the reference electrode, and a fourth electromotive force between the second ion selective electrode and the reference electrode; and the resistance measuring unit determines, from the first electromotive force, the second electromotive force, the third electromotive force, the fourth electromotive force, and a resistance value of the resistor, a resistance value of the first ion selective electrode and a resistance value of the second ion selective electrode.

12. A method of measuring a direct-current resistance of a plurality of ion selective electrodes in an electrolyte concentration measuring apparatus provided with the plurality of ion selective electrodes and one reference electrode, the method comprising:

measuring an electromotive force between at least one of the plurality of ion selective electrodes and the reference electrode;

measuring a voltage and a current between the at least one of the plurality of ion selective electrodes and the reference electrode; and determining the direct-current resistance from the electromotive force, the voltage, and the current.

13. A method of measuring a direct-current resistance of a plurality of ion selective electrodes in an electrolyte concentration measuring apparatus provided with the plurality of ion selective electrodes and one reference electrode, the method comprising:

measuring an electromotive force between at least one of the plurality of ion selective electrodes and the reference electrode;

measuring a voltage and a current between two of the plurality of ion selective electrodes; and determining a sum of resistance values of the two ion selective electrodes from the electromotive force, the voltage, and the current as the direct-current resistance.

* * * * *